United States Patent
Vuyisich et al.

(10) Patent No.: US 12,084,652 B2
(45) Date of Patent: Sep. 10, 2024

(54) METHODS AND COMPOSITIONS FOR PROCESSING SAMPLES CONTAINING NUCLEIC ACIDS

(71) Applicant: Viome Life Sciences, Inc., Bellevue, WA (US)

(72) Inventors: Momchilo Vuyisich, Bothell, WA (US); Andrew Hatch, Santa Fe, NM (US); Ryan Toma, Los Alamos, NM (US); Brittany Twibell, Santa Fe, NM (US); James Horne, Los Alamos, NM (US); Kinga Canfield, Los Alamos, NM (US)

(73) Assignee: Viome Life Sciences, Inc., Bellevue, WA (US)

( * ) Notice: Subject to any disclaimer, the term of this patent is extended or adjusted under 35 U.S.C. 154(b) by 0 days.

(21) Appl. No.: 17/705,115

(22) Filed: Mar. 25, 2022

(65) Prior Publication Data

US 2022/0348987 A1    Nov. 3, 2022

Related U.S. Application Data

(63) Continuation of application No. 16/191,337, filed on Nov. 14, 2018, now abandoned.

(60) Provisional application No. 62/652,613, filed on Apr. 4, 2018, provisional application No. 62/586,649, filed on Nov. 15, 2017.

(51) Int. Cl.
  *C12N 15/10*   (2006.01)
  *C12Q 1/6844*  (2018.01)
  *C12Q 1/6869*  (2018.01)
  *C12Q 1/689*   (2018.01)
  *C40B 40/06*   (2006.01)
  *C40B 40/08*   (2006.01)

(52) U.S. Cl.
  CPC ..... *C12N 15/1068* (2013.01); *C12N 15/1065* (2013.01); *C12N 15/1093* (2013.01); *C12N 15/1096* (2013.01); *C12Q 1/6844* (2013.01); *C12Q 1/689* (2013.01); *C40B 40/06* (2013.01); *C40B 40/08* (2013.01); *C12Q 1/6869* (2013.01)

(58) Field of Classification Search
  CPC ........... C12N 15/1068; C12N 15/1093; C12N 15/1065; C12N 15/1096; C12Q 1/6844; C12Q 1/689; C12Q 1/6869; C40B 40/06; C40B 40/08
  See application file for complete search history.

(56) References Cited

U.S. PATENT DOCUMENTS

| | | | |
|---|---|---|---|
| 5,766,889 A * | 6/1998 | Atwood | C12Q 1/6816 536/25.32 |
| 2015/0329891 A1 | 11/2015 | Tan et al. | |
| 2019/0153438 A1 | 5/2019 | Vuyisich et al. | |

FOREIGN PATENT DOCUMENTS

| | | |
|---|---|---|
| WO | 2017044574 A1 | 3/2017 |
| WO | 2017048993 A1 | 3/2017 |
| WO | 2017176896 A1 | 10/2017 |
| WO | 2019099574 A1 | 5/2019 |

OTHER PUBLICATIONS

Reck et al. (BMC Genomics, 2015, 16(1): 494, 18 pages).*
Kralik et al. (Front. Microbiol. 2017, 8:108, 9 pages).*
Life Technologies ("Real-time PCR handbook", 2012, 70 pages).*
Clontech Laboratories, Inc., Quick-Clone CDNA User Manual, Technical Manual [online], May 25, 2007 [Retrieved Dec. 26, 2018], Retrieved from Internet: , 8 pages.
Hosomichi et al., A Bead-based Normalization for Uniform Sequencing depth (beNUS) protocol for multi-samples sequencing exemplified by HLA-B, 2014 15:645, 9 pages.
International Search Report and Written Opinion for PCTUS18/61130 dated Jan. 11, 2019, 8 pages.

\* cited by examiner

*Primary Examiner* — Kaijiang Zhang
(74) *Attorney, Agent, or Firm* — Morgan, Lewis & Bockius LLP

(57) ABSTRACT

Provided herein are methods and composition for processing samples that contain nucleic acids, or cells containing nucleic acids, of a microbiome, using amounts of primers within a range of mole values and rounds of polymerase chain reaction (PCR) within a range of numbers of rounds.

11 Claims, 9 Drawing Sheets

METHODS AND COMPOSITIONS FOR PROCESSING SAMPLES CONTAINING NUCLEIC ACIDS

REFERENCE TO RELATED APPLICATIONS

This application is a continuation of U.S. application Ser. No. 16/191,337, filed Nov. 14, 2018, which claims the benefit of U.S. Provisional Application No. 62/652,613, filed Apr. 4, 2018, and U.S. Provisional Application No. 62/586,649, filed Nov. 15, 2017, which applications are incorporated herein by reference.

BACKGROUND

In various applications, it can be useful to control and/or quantify the amount, e.g., the molar amount, of nucleic acid in a sample. In high throughput sequencing methods, nucleic acid libraries produced from each of a plurality of different samples may be pooled and sequenced together, for the sake of economy. Typically, in such situations, the libraries are indexed with barcodes so that polynucleotides from different libraries can be distinguished upon sequencing.

It may be useful to achieve molar concentrations of nucleic acids in different libraries that are equimolar or that are related as a known ratio of molarities. Ultimately, a pool comprising different libraries is produced, each library in the pool having a molar amount of nucleic acids that is equal to other libraries, or related to other libraries in a known molar ratio

SUMMARY

In one aspect, provided herein are methods and compositions for achieving molar concentrations of nucleic acids in different libraries that are equimolar or that are related as a known ratio of molarities.

Provided herein are methods of amplifying nucleic acids comprising a) performing a plurality of primer extension reactions on nucleic acid molecules in each of a plurality of separate nucleic acid samples containing nucleic acids, using first polynucleotide primers to initiate primer extension in each sample, wherein: 1) each of the plurality of samples is provided with a fixed molar amount of first primer; 2) the fixed molar amount of first primer in each sample is the same or substantially the same, or is related to the molar amount in other samples in a known ratio; and 3) the plurality of primer extension reactions in each sample is such that, upon completion of the plurality of primer extension reactions, all first primer in each sample has been used to produce amplified nucleic acids. The molar amount of first primer in the samples may be the same or substantially the same. The method can further comprise using a second polynucleotide primer, wherein the second primer is present in equal or substantially equal molar amount as the first primer, or in a known greater molar amount as the first primer. The second primer may be present in equal or substantially equal molar amount as the first primer, and after the plurality of primer extension reactions the molar amount of amplified nucleic acid may be equal to or substantially equal to the molar amount of first and/or second primer. The first and second primers can be different. The first and the second primers can be the same. In certain embodiments, the method further comprises b) combining a portion of each of the plurality of separate samples to provide a pooled sample comprising a library of amplified nucleic acids, wherein the molar amount of amplified nucleic acid from each separate sample in the pooled sample is the same or substantially the same, or related to the molar amounts of other nucleic acids in the pooled sample in a known ratio, thus producing a pooled nucleic acid library. In some cases, the portion of at least one of the plurality of samples is all of the sample. In some cases, the portion of at least two of the plurality of samples is the same. In some cases, the portions of at least two of the plurality of samples is different. The plurality of primer extension reactions can comprise a plurality of rounds of polymerase chain reaction (PCR) amplification, loop-mediated isothermal amplification (LAMP), reverse transcription loop-mediated isothermal amplification (RT-LAMP), strand-displacement amplification (SDA), helicase-dependent amplification (HDA), or transcription-mediated amplification (TMA). In certain embodiments, the nucleic acid molecules in the plurality of separate samples comprise DNA molecules, for example cDNA molecules. In certain embodiments, the nucleic acid molecules in the plurality of separate samples comprise RNA molecules. In certain embodiments, the amplified nucleic acids comprise a sample barcode comprising a predetermined nucleotide sequence, wherein the barcode is different for each different nucleic acid sample. In certain embodiments, the plurality of samples comprises at least 2, at least 5, at least 10, at least 20, at least 50, or at least 100 separate samples.

Also provided herein are methods for amplifying nucleic acids comprising: a) providing a plurality of samples comprising RNA; b) performing a first round of cDNA synthesis on the RNA in the samples to produce a library of first strand cDNA molecules; c) performing a second round of cDNA synthesis on the cDNA strand produced in the first round to provide second strand cDNA molecules, wherein the second strand cDNA molecules comprise a first primer binding site for a first primer and a template for a second primer binding site for a second primer; and d) amplifying the cDNA produced in step c) by providing each of the plurality of samples a molar amount of first primer and second primer, wherein the molar amount of the second primer is equal to or substantially equal to the molar amount of the first primer, or is greater than the molar amount of the first primer in a known amount, and performing a plurality of primer extension reactions, wherein 1) the molar amount of first primer in each of the plurality of samples is the same or substantially the same, or is related to the molar amount in other samples in a known ratio; and 2) wherein the molar amount of first primer in each sample is such that, upon completion of the plurality of primer extension reactions, all first primer in each sample has been used. The first primer can comprise a first polynucleotide sequence and the second primer can comprise a second polynucleotide sequence, wherein the first and second polynucleotide sequences are the same, and wherein the molar amount of first and second primer in each sample is the same. At least one of the primers can comprise sequencing platform-specific adapter sequences; the sequencing platform specific sequences comprise one or more of a sequencing primer hybridization site, a sample barcode and a cluster primer binding site. The method can further comprise e) preparing a pooled nucleic acid library by combining a portion of each of the plurality of samples comprising amplified nucleic acid. In some cases, the portion of at least one of the samples comprises all of the sample. The method can further comprise f) sequencing the amplified nucleic acids in the pooled library. The primer extension reactions can comprise a plurality of rounds of PCR, LAMP, RT-LAMP, SDA, HDA, or TMA. In some cases, the predetermined molar amount of first primer in each of the plurality of samples is the same or substantially the same.

Also provided herein are methods comprising a) providing a plurality of separate samples wherein each sample comprises adapter-tagged polynucleotides, wherein the adapter-tagged polynucleotides comprise a polynucleotide insert flanked by adapter sequences comprising first primer binding sites; b) amplifying the adapter-tagged polynucleotides in each of the plurality of samples using primers in each sample that bind to the first primer binding sites and performing a plurality of primer extension reactions to produce amplified polynucleotides, wherein the first primer added to each sample is added in a predetermined molar amount, wherein 1) the molar amount of first primer in each sample is the same or substantially the same, or is related to the molar amount in other samples in a known ratio; and 2) the molar amount of first primer in each sample is such that, upon completion of the plurality of primer extension reactions, all first primer in each sample has been used. The method can further comprise c) combining a portion of each of the plurality of separate samples to provide a pooled sample comprising a library of amplified nucleic acids, wherein the molar amount of each different amplified nucleic acid in the library is the same or substantially the same, or related to the molar amounts of other amplified nucleic acids in the library in a known ratio, thus producing a pooled nucleic acid library. The portion of at least one of the samples can comprise all of the sample. In certain embodiments, providing adapter-tagged polynucleotides comprises performing primer extension of polynucleotides using primers comprising adapter sequences or ligating adapters to double stranded polynucleotides. In some cases, the adapter-tagged polynucleotides further comprise a second primer binding site for a second primer, and wherein the second primer is added in equal or substantially equal amount as the first primer, or in known greater molar amount as the first primer. The first and second primer binder sites can comprise the same binding sequence and the first and second primers can bind to the binding sequence, and the first and second primers can be present in the same or substantially the same molar amount. In some cases, the adapter sequences comprise sample barcodes. In some cases, the polynucleotides comprise adapter sequences comprising sequencing platform-specific sequences necessary and/or sufficient for sequencing the amplified polynucleotides; the sequencing platform-specific sequences can comprise one or more of a sequencing primer hybridization site, a sample barcode and a cluster primer binding site. In some cases the method further comprises d) sequencing amplified nucleic acids in the nucleic acid library.

Further provided herein are methods comprising a) preparing a set of nucleic acid libraries by amplifying nucleic acids in a plurality of separate samples comprising nucleic acids so that the amplified nucleic acids are present in each of the plurality of separate samples in the same or substantially the same molar amount, or are present in molar amounts in known ratios to each other; and b) combining a portion of each of the separate samples to produce a pool of nucleic acid libraries in which the molar amounts of amplified nucleic acids from each nucleic acid library in the pool are the same or substantially the same, or are present in molar amounts in known ratios to each other. The portion of at least one of the samples can comprise all of the sample. The method can further comprise c) sequencing the nucleic acids in the pool of nucleic acid libraries. In some cases, the amplified nucleic acids in the separate samples comprise a barcode, wherein the barcode for any nucleic acid library is the same for nucleic acids in that library and different from the barcodes for other nucleic acid libraries.

Further provided herein are methods of producing a nucleic acid library comprising a) providing a plurality of samples comprising nucleic acids; b) adding adapter sequences to the nucleic acids in each sample, wherein the adapter sequences comprise primer binding sites, and wherein the nucleotide sequence of the primer binding sites of the adapters are different for each sample; c) combining a portion or all of the samples to produce a pooled sample; d) performing a plurality of primer extension reactions on nucleic acid molecules in the pooled sample, using primers specific to the primer binding sites of the adapters, wherein the different primers are present in equal or substantially equal molar amounts, or in known ratios of molar amounts, wherein the plurality of primer extension reactions is sufficient to use all or substantially all of the primers to produce amplified nucleic acids; thereby producing a final sample in which the amplified nucleic acids from the different original samples are present in the same or substantially the same molar amounts, or in molar amounts of known ratio. The adapter sequences can further comprise a barcode, wherein the barcode is different for each sample. The adapter sequences can further comprise sequencing platform-specific adapter sequences Also provided herein are compositions.

In certain embodiments, provided herein is a set of a plurality of separate nucleic acid libraries, wherein: a) each library comprises polynucleotides; and b) molar amounts of polynucleotide molecules from each nucleic acid library in the set are the same or substantially the same, or are related as a known ratio to each other. In certain embodiments, each separate nucleic acid library is in a separate container. The set may also be distinguished in that b) the polynucleotides comprise a sample barcode, and polynucleotides in any library have the same sample barcode; and c) sample barcodes in different libraries are different. In certain embodiments, the molar amounts of polynucleotide molecules in each library are the same or substantially the same. In certain embodiments the polynucleotides comprise RNA. In certain embodiments the polynucleotides comprise DNA.

In certain embodiments, provided herein is a kit comprising a plurality of sets of polynucleotide primers, wherein each set is contained in a separate container or containers from the other sets, and wherein each set comprises first polynucleotide primers and second polynucleotide primers, wherein: a) the molar amount of the first polynucleotide primers in each set is equal or substantially equal, or is in known ratio to the molar amount of first polynucleotide primers in other sets; and b) the molar amount of the second primer in each set is equal to or substantially equal to the molar amount of the first primer in that set, or greater than the molar amount of the first primer in that set by a known amount. The first primer and the second primer can have different polynucleotide sequences. The first primer and the second primer can have the same polynucleotide sequences and the first and second primers can be present in equimolar concentrations. The kit can further comprise reagents for performing nucleic acid amplification, such as reagents for PCR, LAMP, RT-LAMP, SDA, HDA, or TMA. In some cases, the first polynucleotide primers and the second polynucleotide primers for each set of primers are contained in the same container. In some cases, the first polynucleotide primers and the second polynucleotide primers for each set of primers are contained in different containers.

In certain embodiments, provided herein is a kit comprising a) a plurality of sets of polynucleotide adapters comprising primer binding sites, wherein each set is contained in a separate container from the other sets, and b) one or more primers for binding to the primer binding sites for nucleic acid amplification. The primer binding sites of each set of polynucleotide adapters can the same. The primer or primers can be contained in a single container. The kit can further comprise reagents for performing nucleic acid amplification, such as reagents for PCR, LAMP, RT-LAMP, SDA, HDA, or TMA.

In another aspect, provided herein are methods and compositions for normalizing nucleic acids in different libraries by using detectable labels.

Provided herein is a method comprising: a) performing one or a plurality of primer extension reactions on nucleic acid molecules in a sample using polynucleotide primers, at least a portion of which polynucleotide primers bear a detectable label, to produce a nucleic acid library comprising synthesized nucleic acids, at least a portion of which synthesized nucleic acids incorporate the detectable label; and b) measuring an amount of detectable label incorporated into synthesized nucleic acids in the library, wherein amount of incorporated label indicates an amount of synthesized nucleic acids in the library. In one embodiment no more than one primer extension reaction uses polynucleotide primers bearing a detectable label. In another embodiment the primer extension reaction using labeled polynucleotide primers performs first strand synthesis of a first cDNA molecule from an RNA molecule. In another embodiment all or substantially all of the polynucleotide primers bear the detectable label. In another embodiment no more than 75% of the polynucleotide primers bear the detectable label. In another embodiment a plurality of the primer extension reactions use polynucleotide primers bearing the detectable label. In another embodiment the plurality of primer extension reactions comprise a plurality of rounds of PCR amplification. In another embodiment the method further comprises before determining, separating unincorporated labeled primers from the synthesized nucleic acids. In another embodiment the detectable label is an optical label. In another embodiment the detectable label is a fluorescent label. In another embodiment the fluorescent label is phycoerythrin. In another embodiment the detectable label is a fluorescent label and quantifying comprises inducing fluorescence from the fluorescent label and measuring fluorescence. the synthesized nucleic acids comprise cDNA sequences. In another embodiment the synthesized nucleic acids comprise a sample barcode comprising a predetermined nucleotide sequence. In another embodiment the method further comprises cleaving the incorporated detectable label from the synthesized nucleic acids. In another embodiment primers are provided in pairs comprising forward primers and reverse primers, and only one member of a pair comprises the detectable label. In another embodiment more than 50% of the primers comprise the detectable label. In another embodiment no more than 50%, no more than 25%, no more than 10% or no more than 5% of the primers comprise the detectable label. In another embodiment the method further comprises: c) preparing a sample comprising the nucleic acid library, wherein the nucleic acid library comprises a predetermined amount of the synthesized nucleic acids, e.g., an amount normalized with respect to at least one other nucleic acid library. In another embodiment the synthesized nucleic acid molecules in the nucleic acid library comprise at least one sample barcode. In another embodiment the detectable label is removed from the synthesized nucleic acids before or after normalizing. In another embodiment the method is performed on a plurality of different samples comprising nucleic acid to produce a plurality of nucleic acid libraries, and the method further comprises: c) preparing a pooled, normalized nucleic acid library comprising normalized amounts of synthesized nucleic acids from the plurality of nucleic acid libraries. In another embodiment nucleic acid molecules in each nucleic acid library comprise a sample barcode and wherein the sample barcodes are different between different samples. In another embodiment the detectable label is removed from the synthesized nucleic acids before or after preparing the pooled, normalized nucleic acid library. In another embodiment the plurality of samples is at least 10, at least 20, at least 50, or at least 100. In another embodiment preparing the pooled, normalized nucleic acid library comprises preparing a plurality of normalized nucleic acid libraries and pooling same volumes of the normalized libraries. In another embodiment preparing the pooled, normalized nucleic acid library comprises pooling different volumes of a plurality of libraries, wherein each volume comprises equimolar amounts of nucleic acid.

Also provided herein is a method comprising: a) providing a sample comprising RNA; b) performing first strand cDNA synthesis on the RNA using first primers to produce a library of first strand cDNA molecules, wherein the primers comprise sequencing platform-specific adapter sequences and at least a portion of the primers comprise a detectable label; c) quantifying an amount of first strand cDNA molecules in the library by measuring an amount of the detectable label incorporated in the cDNA, wherein the amount of cDNA is a function of the amount of incorporated label. In one embodiment the sequencing platform specific sequences comprise one or more of a sequencing primer hybridization site, a sample barcode and a cluster primer binding site. In another embodiment performing first strand synthesis further comprises, after primer extension, extending the first strand using a template molecule that hybridizes to the first strand and that comprises sequencing platform-specific adapter sequences. In another embodiment the method further comprises: d) preparing a normalized nucleic acid library comprising an amount of first strand cDNA molecules normalized to predetermined amount. In another embodiment the method further comprises: d) sequencing the first strand cDNA molecules, e.g., without further amplification.

Further provided herein is a method comprising: a) quantifying, according to any method provided herein, amounts of second strand cDNA molecules in each of a plurality of nucleic acid libraries; and b) preparing a pool of normalized nucleic acid libraries in which the amounts of second strand cDNA molecules from each nucleic acid library in the pool are normalized with respect to one another. In one embodiment the method further comprises: c) sequencing the pool of normalized nucleic acid libraries. In another embodiment sequencing is performed without amplification of the normalized nucleic acid libraries in the pool. In another embodiment the normalized nucleic acid libraries in the pool are amplified before sequencing.

Further provided herein is a method for comprising: a) providing a sample comprising adapter-tagged polynucleotides, wherein the adapter-tagged polynucleotides comprise a polynucleotide insert flanked by adapter sequences comprising first primer binding sites; b) amplifying the adapter-tagged polynucleotides using primers to produce a nucleic acid library of amplified polynucleotides, wherein at least a portion of the primers comprise a detectable label and wherein at least a portion of the amplified polynucleotides incorporate the detectable label; and c) quantifying an amount of amplified polynucleotides in the nucleic acid library by measuring an amount of the detectable label incorporated in the amplified polynucleotides, wherein the amount of amplified polynucleotides is a function of the amount of incorporated label. In one embodiment providing adapter-tagged polynucleotides comprises performing primer extension of polynucleotides using primers comprising adapter sequences or ligating adapters to double stranded polynucleotides. In another embodiment the first primer binding sites comprise a first forward primer binding site and a first reverse primer binding site, wherein the first forward primer binding site and the first reverse primer binding site are the same or different. In another embodiment the primers comprise a first primer set and a second primer set, wherein: (i) primers in the first primer set comprise sequences that bind to the first primer binding sites and further comprise second primer binding sites comprising a second forward primer binding site and a second reverse primer binding site, wherein the second forward primer binding site and the second reverse primer binding site are the same or different; and (ii) primers in the second primer set comprise sequences that bind to the second primer binding sites, and wherein at least a portion of the primers in the second primer set comprise the detectable label. In another embodiment the first set and second set of primer pairs are present in amounts having relative ratios between about 2:1 to about 1:2, e.g., about 1:1. In another embodiment: (i) the first forward and reverse primer binding sites are different; and (ii) the second forward and reverse primer binding sites are different. In another embodiment the first set of primers comprise sample barcodes. In another embodiment the amplified polynucleotides comprise adapter sequences comprising sequencing platform-specific sequences necessary and/or sufficient for sequencing the amplified polynucleotides. In another embodiment the sequencing platform specific sequences comprise one or more of a sequencing primer hybridization site, a sample barcode and a cluster primer binding site. In another embodiment the method further comprises: d) preparing a normalized nucleic acid library comprising an amount of amplified polynucleotides normalized to a predetermined amount. In another embodiment the method further comprises: e) sequencing amplified polynucleotides in the nucleic acid library.

Further provided herein is a method comprising: a) quantifying, according to any method as provided herein, amounts of amplified polynucleotides in each of a plurality of nucleic acid libraries; and b) preparing a pool of normalized nucleic acid libraries in which the amounts of amplified polynucleotides from each nucleic acid library in the pool are normalized with respect to one another. In another embodiment the method further comprises: c) sequencing the pool of normalized nucleic acid libraries.

Further provided herein is a pool of normalized nucleic acid libraries, wherein: a) each library comprises polynucleotides, at least a portion of which polynucleotides in each library comprise a detectable label; b) polynucleotides in any library have the same sample barcode; c) sample barcodes in different libraries are different; d) amounts of polynucleotide molecules from each nucleic acid library in the pool are normalized with respect to one another.

Further provided herein is a collection of nucleic acid libraries, each library contained in a different container, wherein at least a portion of polynucleotides in each library comprises a detectable label. In another embodiment polynucleotides in each nucleic acid library comprise a sample barcode that distinguishes polynucleotides in one nucleic acid library from those in another nucleic acid library. In another embodiment amounts of polynucleotides in each library are normalized with respect to each other.

Further provided herein is a kit comprising: a) a first primer set comprising primers comprising sequences that bind to first primer binding sites and comprising a detectable label; and (b) a second primer set comprising primers having the same nucleotide sequence as primers in the first set, and not comprising a detectable label; wherein the ratio of primers in the first set to primers in the second set is between about 1:100 to 100:1, between about 10:1 to 1:10, between about 1:5 to 5:1, between about 1:3 to 3:1, between about 1:2 to 2:1 or about 1:1, or wherein there are fewer primers in the first primer set than in the second primer set. In one embodiment the kit further comprises a template polynucleotide comprising a 3' terminal nucleotide sequence that binds to an overhang produced by a polymerase, wherein the template polynucleotide comprises a primer binding site. In another embodiment the kit further comprises a reverse transcriptase. In another embodiment the kit further comprises reagents for performing primer extension, including nucleotides and buffers. In another embodiment the kit further comprises one or more containers that contain the first primer set and the second primer set in the same or separate containers.

Further provided herein is a kit comprising first polynucleotide adapters and second polynucleotide adapters, wherein: (a) the first polynucleotide adapters comprise (i) first binding sequences for binding to a target primer binding site and (ii) primer binding sites for binding to binding sequences on the second polynucleotide adapters, wherein the first polynucleotide adapters do not comprise a detectable label; and (b) the second polynucleotide adapters comprise second binding sequences for binding to the primer binding sites on the first polynucleotide adapters, wherein at least a portion of the second polynucleotide adapters comprise a detectable label. In one embodiment the first polynucleotide adapters comprise forward primers and reverse primers, wherein the forward primers comprise forward binding sequences and forward primer binding sites and the reverse primers comprise reverse binding sequences and forward primer binding sites; and the second polynucleotide adapters comprise forward primers and reverse primers, wherein the forward primers comprise forward primer binding sequences and the reverse primers comprise reverse binding sequences. In another embodiment the kit further comprises reagents for performing PCR, including a DNA polymerase, nucleotides and buffers. In another embodiment the first primer set and the second primer set are contained in the same or separate containers.

Other objects of the disclosure may be apparent to one skilled in the art upon reading the following specification and claims.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

I. Definitions

Figure 1:
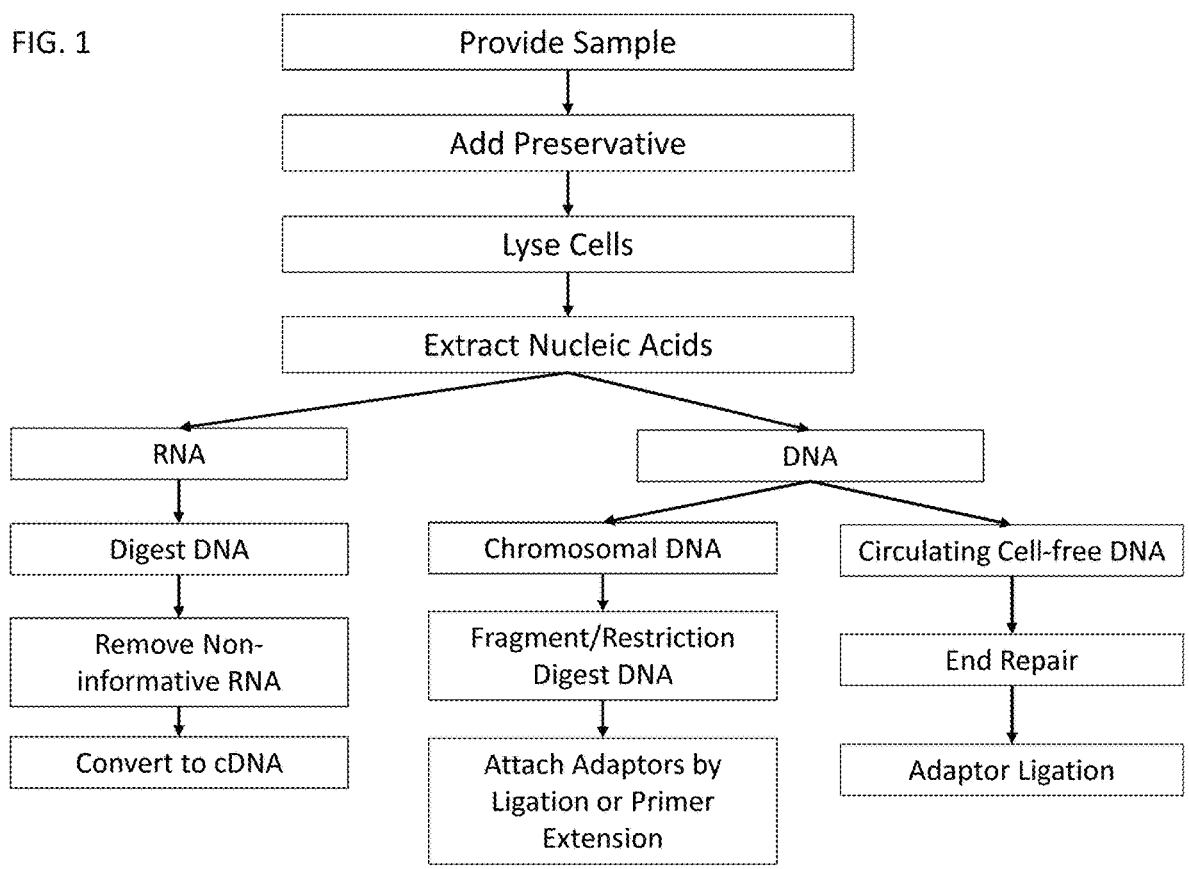
FIG. 1 shows an exemplary protocol for preparing nucleic acids for primer extension by the methods disclosed herein.

As used herein, the term "sample" includes a composition comprising an analyte. A sample can be a raw sample, in which the analyte is mixed with other materials in its native form (e.g., a source material), a fractionated sample, in which an analyte is at least partially enriched, or a purified sample in which the analyte is at least substantially pure.

As used herein, a chemical entity, such as a polynucleotide or polypeptide, is "substantially pure" if it is the predominant chemical entity of its kind in a composition. This includes the chemical entity representing more than 50%, more than 80%, more than 90% or more than 95% or of the chemical entities of its kind in the composition. A chemical entity is "essentially pure" if it represents more than 98%, more than 99%, more than 99.5%, more than 99.9%, or more than 99.99% of the chemical entities of its kind in the composition. Chemical entities which are essentially pure are also substantially pure.

As used herein, the term "subject" includes an individual organism, e.g., an animal, a plant or a microbe. Animal subjects include, without limitation, human and nonhuman animals. Nonhuman animals may be mammals, birds, fish, reptiles and insects. Nonhuman animals include, for example, bovines, swine, horses, sheep, goats, chickens, turkeys, dogs, cats and birds.

As used herein, the term "host" includes an organism hosting a microbial community.

As used herein, the term "microbiome" includes a microbial community comprising one or a plurality of different microbial strains or species inhabiting a host.

As used herein, the terms "polynucleotide" and "nucleic acid" are used interchangeably and include both single-stranded and double-stranded molecules. As used herein, the term "oligonucleotide" includes short polynucleotides, e.g., no more than 500 nucleotides in length. In certain embodiments, a polynucleotide can comprise natural or non-natural nucleotides, such as peptide nucleic acids or locked nucleic acids.

As used herein, "cell-free nucleic acid" (e.g., "cell-free DNA" ("cfDNA") or "cell-free RNA") includes nucleic acid not encapsulated in a cell and found in in a bodily fluid, such as blood/serum/plasma, urine, amniotic fluid, saliva, pleural effusion, bronchial lavage or aspirates, breast milk, colostrum, tears, seminal fluid, peritoneal fluid, and stools. Typically, cell-free DNA comprises DNA having a size range between about 140 and about 180 nucleotides.

As used herein, the term "adapter" includes a polynucleotide comprising adapter sequences comprising, at least, a primer binding site, e.g., a universal primer binding site or a forward or reverse primer binding site. Adapters also can comprise other elements including, without limitation, a sample barcode, a molecular barcode, a sequencing primer binding site (which may also serve as an amplification primer binding site) or a binding site for binding polynucleotide to platform hardware, such as a flow cell probe binding site. In certain embodiments, adapters can comprise non-complementary ends. These include, for example, "Y-shaped" adapters or adapters which fold back upon themselves to form looped structures. Y-shaped adapters, in particular, can be useful when different strands ("Watson" and "Crick" strands) of a double stranded nucleic acid need to be distinguished. Depending on context, the term "adapter" may also refer to a nucleotide sequence comprising adapter elements.

As used herein, the term "adapter-tagged polynucleotide" includes a polynucleotide comprising a nucleic acid insert flanked on one or both ends by adapter sequences bearing a primer binding site.

As used herein, the term "nucleic acid library" includes a collection of nucleic acids, for example, a collection of adapter-tagged polynucleotides. Typically, polynucleotide members of a nucleic acid library comprise a sample index. Optionally, they may comprise molecular barcodes useful for distinguishing individual molecules from each other, either using the barcode, alone, or in combination with insert sequence information.

As used herein, the term "primer binding site" includes a nucleotide sequence to which a polynucleotide primer can hybridize, e.g., for PCR or primer extension.

As used herein, the term "primer" includes a polynucleotide, typically an oligonucleotide, having a sequence ("binding sequence") that binds to a primer binding site. Primers are typically categorized as "universal primers" or "degenerate primers". Primers are used for primer extension and PCR. In amplification, such as PCR, primers bind to primer binding sites on each strand of a double stranded nucleic acid molecule with a target sequence (amplicon) positioned between them. In certain embodiments, for example, when the primer binding site on the first strand of a double stranded molecule is different than the primer binding site on a second, complementary, strand, primers are provided as a set of two primers ("primer pair"). Primers in the primer pair may be differentiated as a "forward primer" and a "reverse primer".

As used herein, the term "universal primer" includes a primer having a binding sequence that binds to a primer binding site on an adapter. Accordingly, a universal primer can be used to amplify all adapter-tagged polynucleotides in a sample.

As used herein, the term "degenerate primer" includes a mixture of primers having a substitution of different nucleotides at the binding sequence. For example, degenerate primers can have a degenerate hexamer nucleotide sequence.

As used herein, the term "barcode" includes a nucleotide sequence which provides information about the polynucleotide in which the barcode is incorporated. A barcode may provide information specific to a single molecule or collection of molecules. Barcodes are typically provided in polynucleotide adapters. Barcodes typically have sequences of no more than 100, 50, 20 or 10 nucleotides.

As used herein, the term "sample barcode" includes a barcode that distinguishes polynucleotides sourced from a first sample from polynucleotides sourced from a second, different sample. Accordingly, sample barcodes in an ensemble of adapters will be the same in each sample and different between different samples. For example, polynucleotides sourced from each of 50 different samples may comprise 50 different sample barcodes.

As used herein, the term "molecular barcode" includes a barcode that, alone or in combination with other information, distinguishes different molecules in a sample from each other. For example, a set of molecular barcodes may have sufficient diversity such that substantially all molecules in a sample bear a different molecular barcode. A collection of such polynucleotides is referred to as being "uniquely tagged". Alternatively, a set of barcodes may have a diversity that is less than the number of polynucleotides in a sample. In this case, different molecules that bear the same molecular tag may be distinguished based on information derived from the sequence of the insert. A collection of such polynucleotides is referred to herein as being "non-uniquely tagged".

As used herein, the term "index" includes one or more pieces of information, such as barcodes, which, alone or in combination, provide information. For example, an adapter-tagged polynucleotide can comprise a single sample barcode and/or molecular barcode, or a plurality of sample barcodes or molecular barcodes, e.g., attached at each end. A single barcode or a collection of barcodes attached to a molecule can function as an "index". Thus, a "sample index" can be defined by one or a plurality (e.g., two) of sample barcodes, and a "molecular index" can be defined by one or a plurality (e.g., two) of molecular barcodes.

As used herein, the term "detectable label" includes a composition detectable by spectroscopic, photochemical, biochemical, immunochemical, chemical, or other physical means. Examples of detectable labels include, without limitation, colorimetric, fluorescent, chemiluminescent, enzymatic, and radioactive labels. A detectable label can produce a signal directly (a "direct label") or indirectly (an "indirect label"). A direct label directly produces a signal. Examples of direct labels are fluorescent labels (e.g., phycoerythrin, fluorescein isothiocyanate, texas red, rhodamine, a green fluorescent protein, a red fluorescent protein, a yellow fluorescent protein), luminescent labels (e.g., luminescent proteins such as luciferase), enzymatic labels (e.g., horse radish peroxidase or alkaline phosphatase), colorimetric labels such as colloidal gold or colored glass or plastic (e.g., polystyrene, polypropylene, latex, etc.) beads and radioactive labels (e.g., 3H, 125I, 35S, 14C, or 32P). In one embodiment, the detectable label is a molecular beacon comprising a nucleotide hairpin structure having tethered to its ends a fluorophore and a quencher. An indirect label is a label that is detected (primarily or secondarily) by another moiety comprising a direct label. Examples of indirect labels are capture moieties, such as antibodies, biotin or streptavidin, that bind other molecules which themselves bear a direct label.

Detectable labels can be measured as follows. Fluorescence: A fluorescent molecule (fluorophore), such as a dye or a protein, are excited with light of specific wavelength. The fluorophore then emits light of a specific wavelength, which can be measured using a detector, such as a photomultiplier tube, CMOS, etc. Luminescence: Chemical reactions can produce light. One example is enzyme Luciferase that oxidizes luciferin and emits photons. This light can be measured using a detector, such as a photomultiplier tube, CMOS, etc.

As used herein, the term "high throughput sequencing" includes the simultaneous or near simultaneous sequencing of thousands of nucleic acid molecules. High throughput sequencing is sometimes referred to as "next generation sequencing" or "massively parallel sequencing". Platforms for high throughput sequencing include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing, single molecule real time (SMRT) sequencing (PacBio), and nanopore DNA sequencing (e.g., Oxford Nanopore).

As used herein, the term "kit" includes a collection of items intended for use together. The items in the kit may or may not be in operative connection with each other. A kit can comprise, e.g., reagents, buffers, enzymes, antibodies and other compositions specific for the purpose. A kit can also include instructions for use and software for data analysis and interpretation. A kit can further comprise samples that serve as normative standards. Typically, items in a kit are contained in primary containers, such as vials, tubes, bottles, boxes or bags. Separate items can be contained in their own, separate containers or in the same container. Items in a kit, or primary containers of a kit, can be assembled into a secondary container, for example a box or a bag, optionally adapted for commercial sale, e.g., for shelving, or for transport by a common carrier, such as mail or delivery service.

As used herein the term "substantially," in phrases such as "substantially equal" or "substantially equimolar," includes measurements or procedures in which, for example, two different samples are found to have the same nucleic acid concentration, within measurement error, or are produced by methods which should lead to the same nucleic acid concentration (molar concentration) if reactions proceed to completion. It will be appreciated that minor variations in, for example, concentration, are still within the meaning of "substantially equal," for example, if such variations do not affect the use of samples or interpretation of data from samples.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or."

II. Introduction

Provided herein are methods and compositions for manipulating polynucleotide samples during amplification, to provide equimolar amounts of polynucleotides in samples, or molar amounts that are related in a known ratio, or to normalize the polynucleotide concentrations in various samples by using a detectable label when amplifying the samples. Each technique will be described in turn.

III. Preparation of Polynucleotides from Samples

For both methods, preparation of preparation of polynucleotides from samples are used. Methods of producing pooled, concentration adjusted (e.g., normalized) nucleic acid libraries involve providing libraries from a plurality of samples. Accordingly, while methods may describe library preparation with respect to a single sample, it is understood that the procedures can be used on a plurality of samples, for example serially or in parallel.

Referring to FIG. 1, library preparation begins with the provision of polynucleotides, i.e., DNA or RNA, from a sample. Polynucleotides can be sourced from any biological sample. The biological sample can comprise polynucleotides from the genome of a single individual or, in the case of microbiome analysis, a plurality of organisms of different species. Samples used as source material include, without limitation, biological materials from an organism, cultured biological materials (e.g., cultured cells), environmental samples (e.g., water soil or air) or forensic samples (e.g., blood, hair, semen). A biological sample from an organism can comprise, for example, stool, blood, throat swab, nasopharyngeal swab, sputum, cerebral spinal fluid, serum, plasma, urine or a biopsy (e.g., tissue biopsy or liquid biopsy). In embodiments in which analysis of a subject individual's microbiome and/or microbial transcriptome is desired, the sample can be one known to contain microorganisms, e.g., stool.

Polynucleotides can be isolated from a sample by methods well known in the art.

Polynucleotides can be extracted directly from the sample or cells in the sample can first be lysed to release their polynucleotides. Nucleic acid in the sample can be treated with an RNA or DNA preservative, as appropriate, to inhibit degradation of nucleic acid. Polynucleotides can be isolated from a sample by contacting the sample with a solid support comprising moieties that bind nucleic acids. For example, the solid support can be a column comprising silica or can comprise paramagnetic silica beads. After capturing nucleic acids in a sample the beads can be immobilized with a magnet and impurities removed. DNA can be isolated with silica, cellulose, or other types of surfaces, e.g., Ampure SPRI beads. Kits for such procedures are commercially available from, e.g., Promega (Madison, WI) or Qiagen (Venlo, Netherlands). If the target polynucleotide is RNA the sample can be exposed to an agent that degrades DNA, for example, a DNase. For example, the Qiagen RNeasy kit can be used to purify RNA.

Purified nucleic acids may be further fractionated to isolate target sequences or to remove unwanted sequences. For example, in the case of microbiome analysis involving analysis of microbiome RNA (e.g., transcriptome), one may wish to eliminate noninformative RNA from the sample. Noninformative RNA can include, for example, host rRNA and a plurality of the most common host mRNA species in the sample. For example, in human blood, common RNA species include, for example, hemoglobin, myoglobin, 18S and 28S rRNA and 16S and 23S bacterial rRNA. To accomplish this, one can employ oligonucleotide probes that hybridize to the species and that bear at least one extraction moiety (e.g., a biotin moiety).

Alternatively, one may wish to enrich for specific sequences by positive rather than negative selection. In certain embodiments preparation of polynucleotides can include sequence capture which can involve contacting polynucleotides with oligonucleotide probes or baits attached to solid supports. These probes capture polynucleotides having sequences that hybridize to the probe. Captured polynucleotides can be isolated after washing the solid support or supports to remove unbound polynucleotides. This step may be performed after adapter ligation.

DNA can be chromosomal DNA or cell free DNA. Typically, chromosomal DNA is fragmented for processing into a library. For Illumina sequencing, nucleic acid fragments typically have a length between about 100 and 1000 nucleotides.

Adapters can be attached to DNA molecules through ligation or through primer extension of primers comprising adapter sequences using DNA molecules as a template.

Adapter ligation can involve blunt end ligation or overhang ligation. In blunt end ligation in adapter with a blunt end is ligated to a DNA molecule that also comprises a blunt end. In overhang ligation a DNA molecule with an overhang, such as a "A" overhang or an overhang resulting from restriction endonuclease cleavage, is brought into contact with an adapter molecule comprising a complementary overhang.

Polynucleotides subjected to fragmentation or cell free DNA typically comprise ends with single-stranded overhangs that require end repair before adapter ligation. End repair can be accomplished by, for example, an enzyme such as Klenow which cleaves back 5' overhangs and fills in 3' overhangs. The result can be a blunt ended molecule or molecule with a specific overhang.

Alternatively, target polynucleotides can be provided with adapters through a primer extension reaction in which a primer molecule comprises adapter sequences and a sequence that hybridizes to a location in a target polynucleotide. For example, sequence-specific amplification can comprise contacting a DNA sample with primers that hybridize to locations flanking a target sequence. Primers can be extended such that the newly synthesized strand comprises both adapter sequences from the primer and the target sequence upon second strand synthesis in the opposite direction the resulting polynucleotides will comprise a target sequence flanked by adapter sequences. Accordingly, such amplification can comprise multiplex amplification in which a plurality of target sequences is amplified simultaneously.

In the case of chromosomal DNA, the polynucleotides are typically fragmented. In the case of cfDNA, the molecules typically have a size distribution of about 140-180 nucleotides. In either case, molecules are end repaired, by Klenow, to produce either a blunt end or a single nucleotide overhang, e.g., "A".

A restriction site overhang DNA can be prepared for adapter ligation by end repair of polynucleotide molecules.

After at least one round of amplification, template molecules bear adapter-tags.

Purified nucleic acids may then be prepared for the methods disclosed herein.

IV. Methods and Compositions for Primer-Limited Amplification of Nucleic Acids

A. Amplification

Provided herein are methods of providing equal or substantially equal molar amounts of nucleic aids in a plurality of separate samples or in a pooled sample from a plurality of separate samples, and/or of providing molar amounts of nucleic acids in a plurality of separate sample, or in a pooled sample, that are related by known molar ratios. The methods of the first technique generally do not require labeling or reading of labels and can be carried out in a few steps; typically, the methods do not require further procedures after nucleic acid amplification beyond combining samples to pool them. Also provided herein are methods of preparing nucleic acid libraries comprising predetermined molar amounts of nucleic acid, which amounts have been determined, e.g., by methods provided herein. Also provided herein are pooled, nucleic acid libraries comprising normalized amounts of nucleic acid derived from each of a plurality of different samples, e.g., pooled libraries in which nucleic acids from different samples are present in equal molar amounts, or substantially equal molar amounts, and/or in amounts related to each other in known molar ratios. Also provided herein are kits for use in producing the nucleic acid libraries described herein.

Using the methods and compositions described herein, a pooled normalized nucleic acid sample may be produced from a plurality of individual samples in procedures requiring nothing more than amplification of nucleic acids in the individual samples and pooling of portions of the individual samples. I.e., the methods and compositions described herein eliminate the necessity for labeling, reading labels, adjusting concentrations, and the like, that are usually involved in producing normalized libraries, thus eliminating time and costly reagents from the process.

The molar concentration or quantity of polynucleotides, e.g., adapter-tagged polynucleotides, in the sample can be controlled by methods described herein. Typically, the methods involve primer-induced amplification of nucleic acids in a sample using a fixed molar amount of primer, and performing amplification through a sufficient number of rounds that the primer is completely consumed; thus, the final molar amount of nucleic acid in the sample after the final round of amplification will, in general, be related in a known manner to the fixed molar amount of primer, for example, equal or substantially equal to the molar amount of primer, though other possibilities are discussed herein. If a plurality of samples are amplified in this manner, and the samples combined into a pooled sample, the molar amounts of nucleic acid from each sample in the pooled sample can be controlled by controlling the relative amount (volume) of each individual sample used to produce the pooled sample. In certain embodiments, the amplification may occur after individual samples are tagged with adapters and pooled; in these embodiments, adapters used in different samples typically have different primer binding sites, and the molar amounts of amplified nucleic acid produced from each sample is controlled by using fixed molar amount of primer for each of the different primer binding sites.

The methods and compositions provided herein are useful in both DNA and RNA amplification and quantification and/or normalization. After amplification and, e.g., pooling, nucleic acids in the sample may be sequenced, using any suitable sequencing technology.

According to one method, nucleic acid in a sample is amplified in a plurality of primer extension reactions, using primers in a fixed molar amount. After sufficient rounds of amplification, the primer is used up, and the amount of amplified nucleic acid in the sample will be equal to, or substantially equal to, the fixed amount of primer used in the amplification, or will be related to the amount of primer used in a known ratio. A plurality of separate samples may be amplified in this manner, where the final amount of amplified nucleic acid in each sample is known to be equal to, or substantially equal to, the fixed amount of primer used in the amplification in each sample, or related to the amount of primer used in a known ratio. The samples may then be pooled. The relative amount of nucleic acid from each sample that is included in the pooled sample can be controlled by controlling the relative amount (volume) from each sample that is included the pooled sample. Alternatively, samples can be prepared separately with adapter sequences, where the adapter sequences for different samples bear different primer binding sites, then the samples can be pooled and primer extension amplification performed on the pooled sample, where the molar amounts of nucleic acid for each sample are determined by the molar amount of primer used for that sample.

Any suitable method of nucleic acid amplification may be used, including, but not limited to, polymerase chain reaction (PCR) amplification, loop-mediated isothermal amplification (LAMP), reverse transcription loop-mediated isothermal amplification (RT-LAMP), strand-displacement amplification (SDA), helicase-dependent amplification (HDA), or transcription-mediated amplification (TMA). For ease of description, reactions will be discussed in terms of PCR; necessary adjustments for other methods of amplification will be readily apparent to one of skill in the art.

In a nucleic acid amplification method, two primers may be used, e.g., one for each strand of DNA, such as a forward primer and a reverse primer. Nucleic acids in the sample may be prepared, for example, with adapter sequences that contain the primer binding sites for the first primer and the second primer (e.g., on different strands of DNA); in certain cases, the first and second primer binding sites are the same, and thus the first and second primers are the same; in other cases, the first and second primer binding sites are different, and thus the first and second primers are different. In the former case, when a fixed molar amount of primer (which acts as both first and second primer) is added and sufficient rounds of amplification performed, the molar amount of amplified nucleic acid will be half that of the fixed molar amount of primer used, if the amplified nucleic acid is double stranded, or will be equal to or substantially equal to the molar amount of primer used if amplified nucleic acid is single-stranded. In the latter case, typically equal molar amounts of first and second primers are used and after amplification the molar amount of amplified nucleic acid will be equal to or substantially equal to the molar amount of each primer used (as double stranded nucleic acid; if strands are melted or nucleic acid is only single-stranded, e.g., RNA, then the molar amount will be equal to double the molar amount of each primer). If one primer is used in excess, amplification will continue after the limiting primer is used up for double-stranded nucleic acid, and will stop when second primer is consumed to produce single-stranded nucleic acid. For example, in a PCR amplification of double stranded DNA using a first primer for first strand and a second primer for second strand, if first primer is present in a molar amount of 0.1 mole, and second primer is present in a molar amount of 0.15 mole, exponential amplification will occur until the 0.1 mole of first primer is consumed, and 0.1 mole of double-stranded DNA will be produced. After that point, when strands are melted, only the second strand, with the second primer site, will continue to be amplified, with additional strands produced until the 0.15 mole of second primer is consumed. Total molar amounts are 0.1 mole for first strand and 0.15 mole for second strand. These amounts and amplification technique (PCR) are merely exemplary, and amounts and ratios for other amplification techniques will be apparent to one of skill in the art. For example, in certain amplification techniques an indefinite amount of amplified nucleic acid may be produced at one or more steps, and molar amounts of final product may vary depending on conditions used; in such cases, routine experimentation can show the proper conditions to control the reactions sufficiently that separate samples receive the same treatment and produce amounts of nucleic acid in desired ratios.

Any suitable number of rounds of amplification (cycles) may be used, which may be dependent on the type of amplification procedure used. In certain embodiments, e.g., in which PCR is the amplification method, the number of amplification rounds (cycles) is 2-50, or 2-40, or 2-30, or 2-25, or 5-50, or 5-40, or 5-30, or 5-25, or 10-50, or 10-40, or 10-35, or 10-30, or 10-25, or 15-50, or 20-40, or 20-30, or 21-30, or 22-30, or 23-30, or 24-30, or 25-30, or 26-30, or 27-30, or 28-30, or 21-29, or 22-29, or 23-29, or 24-29, or 25-29, or 26-29, or 27-29, or 21-28, or 22-28, or 23-28, or 24-28, or 25-28, or 26-28, or 21-27, or 22-27, or 23-27, or 24-27, or 25-27; for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 rounds of amplification (cycles).

In certain embodiments, a plurality of separate nucleic acid samples are amplified, using fixed molar amounts of primer in each sample. Nucleic acids in each sample may be prepared with adapter sequences with appropriate primer binding sites, as well as, e.g., barcodes (which may be unique to each sample), sequencing platform-specific sequences, etc. The molar amount of primer in each sample may be the same or different. After amplification, the samples may be combined to produce a pooled nucleic acid sample. The relative amounts of nucleic acid from each separate sample that are present in the pooled sample may be controlled by controlling the relative amount (volume) of each sample that is incorporated into the pooled sample. For example, separate samples can be amplified using the same molar amount of primer in each sample, so that after amplification, each sample contains the same or substantially the same molar amount of nucleic acid. If the entire volume of one sample is added to the pooled sample, and only one-tenth of the volume of a second sample is added to the pooled sample, then the nucleic acids from the first sample will be present in the pooled sample in 10:1 molar ratio compared to the nucleic acids from the second sample. Any desired ratio of molar amounts of nucleic acids from separate samples may be produced in the pooled sample by manipulating primer amounts in each separate sample used for amplification, or by manipulating relative portions of each separate sample combined into the pooled sample, or both.

The molar amount of primer added to each sample may be known, in which case the final molar amount of amplified nucleic acid in the sample can be known, and the final molar amount of nucleic acid from that sample in a pooled sample can be known. Alternatively, for example, all or a portion of separate samples, in which primer sites are the same, may use the same primer; a large central batch of primer solution may be prepared, and the relative molar amount of amplified nucleic acid in separate samples amplified using the primer may be determined by the relative amount of the central primer solution added to the separate samples. In this case, the actual molar amount of primer need not be known; so long as each sample goes through sufficient rounds of amplification to use all primer, the relative molar amounts of nucleic acid in each sample will be related according to the relative amount of central primer solution used in each. For example, separate samples containing equal or substantially equal molar amounts of amplified nucleic acids can be produced using the same volume of central primer solution in each. In certain embodiments, a known molar amount of primer is added to each sample, for example, with an exemplary volume for primer addition of 50 μL, the concentration of the primer solution can be 1-500 nanomolar (for a total amount of primer of $5 \times 10^{-14}$ to $2.5 \times 10^{-11}$ mole in a 50 μL portion), or 1-200 nanomolar, or 1-100 nanomolar, or 2-80 nanomolar, or 5-70 nanomolar, or 8-60 nanomolar, or 10-50 nanomolar, or 15-40 nanomolar, or 20-35 nanomolar, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nanomolar (given an exemplary volume of 50 μL the molar amount may be calculated for each). The same molar amount of primer may be added to each sample, or different, known molar amounts of primer, or amounts of primer related to each other in known ratios, may be added to each sample. If a primer pair is used, molar amount can refer to the total of primer or to molar amount of each member of the pair.

In certain embodiments, it is desired to bring the amount of different nucleic acids in a single sample, which may be present at very different levels, to the same or similar levels, or to levels where the different nucleic acids may be detected. For example, a blood sample may contain nucleic acid from two or more viruses, which are present in greatly differing amounts. If the sample is split into separate samples, each of which is amplified with a fixed molar amount of primer (e.g., primer specific for specific viral nucleic acid) through sufficient rounds to use all the primer, then, optionally, combining the amplified samples, viruses present at low levels relative to others can be readily detected.

When separate samples are combined to form a pooled sample, any suitable number of separate samples may be uses, e.g., at least 2, 3, 4, 5, 10, 20, 50, 100, 200, or 500 samples. In certain embodiments, a single sample is split into 2 or more samples which, after amplification, can then be combined into a pooled sample. When samples are pooled, in certain embodiments the pooled sample is treated (after pooling) to remove reaction components from amplification that are not necessary for further analysis and that may interfere with analysis, including but not limited to unincorporated nucleotides, buffer, enzymes, and additives; cleanup protocols are well-known in the art.

In certain embodiments, genomic sequences are desired, and any suitable method for amplifying genomic nucleic acid may be used. In certain embodiments, it is desired to determine transcriptomes or other measures of RNA, in which case any suitable method for amplifying RNA sequences may be used. If, e.g., PCR is to be used, RNA can be subject to first strand synthesis (reverse transcription) to produce cDNA using first primers. In certain embodiments, the primers used during first strand synthesis may comprise nucleotide sequences that are necessary and/or sufficient for sequencing on a specific sequencing platform. The cDNA may include primer binding sites for one or more primers, which may be used in fixed molar amounts during amplification, as described herein. When performed on a plurality of different samples a pool of nucleic acid libraries can be produced in which the amounts of nucleic acids from each library are normalized with respect to each other based at least in part on the amounts primer used for amplification in each sample. The pooled sample can be used to populate a sequencing flow cell. Upon sequencing, quantities of nucleic acid sequences between samples can be compared directly to one another.

Also provided here are normalized nucleic acid libraries, e.g., DNA libraries and pooled, normalized nucleic acid libraries, e.g., DNA libraries in which nucleic acids from different samples are present in known molar ratios to each other.

Using the methods and compositions described herein, any suitable number of different samples may be amplified to provide final concentrations of nucleic acid in the samples that are intended to be equal or substantially equal. It will be appreciated that real-world conditions can cause amplified samples to be at nucleic acid concentrations that are different from the intended concentration; however, using the described methods and compositions it is possible to obtain a relatively narrow range of concentrations. This allows a greater number of samples to be analyzed on an analyzer that takes in a mixture of samples, e.g., a sequencer such as an Illumina sequencer, and remain within quality control (QC) limits. Any suitable range may be set as the QC limit, such as within 100, 90, 80, 70, 60, 50, 40, 30, 20, or 10% of the mean; and a plurality of samples amplified by the methods and compositions of the invention can be within the desired QC range, such as at least 20, 30, 40, 50, 55, 60, 65, 70, 75, 80, 85, 87, 90, 91, 92, 93, 94, 95, 96, 97, 98, or 99% of the samples, for example, at least 70%, such as at least 80% or at least 90%. See Example 3, in which the QC limit for a sequencer was set at within 50% of the mean number of reads per sample, and 93.4% of the samples fell within the QC limit. It will be appreciated that this is merely exemplary, and that any suitable QC limit may be set, with corresponding percentage of samples falling within the limit.

B. Preparation of Nucleic Acid Libraries

Preparation of nucleic acid libraries comprising polynucleotides in known molar ratios can involve creation of adapter tagged polynucleotides. Adapters can be provided by hybridization of primers comprising adapter sequences to target molecules, followed by primer extension, or by ligation of the adapters to nucleic acids in a sample. Primer extension is typically used with single-stranded target nucleic acids. Double stranded nucleic acids can be tagged through primer extension or ligation. Primer extension can be useful to amplify target sequences in long nucleic acid molecules. Ligation of adapter is particularly useful for tagging short, double stranded nucleic acid molecules, such as cell-free DNA.

Methods disclosed herein comprise performing a plurality of primer extension reactions on nucleic acid molecules in a sample, either original, untagged molecules, or adapter-tagged molecules. Primer extension is performed using polynucleotide primers. Primer extension can use a single set of primers or a plurality (e.g., two) primer sets. In the case of a single primer set, all or substantially all of the primer can be used in the primer extension reactions. In the case of multiple primer sets, some or all of the different primers can be used.

The product of primer extension reactions is a nucleic acid library, in which the molar amount of nucleic acids in the library is determined by the molar amount of primer used. This can provide an indication of the amount of nucleic acid in a single library, or the relative amounts of nucleic acids in a plurality of libraries.

In order to quantify nucleic acids in a sample or a library, a known molar amount of primer can be used during amplification. The molar amount of amplified nucleic acid will be related in a known manner to the known molar amount of primer used.

In certain embodiments of the disclosed methods, adapter-tagged molecules comprise sequencing platform-specific sequences compatible with a particular sequencing platform. For example, in the case of Illumina MiSeq devices, platform-specific sequences can include a sequencing primer binding site and a flow cell cluster primer binding site. Preparation of tagged libraries whose molar concentration can be known is not limited to any one technology. For example, this method can be used to prepare PacBio, Ion Torrent, and Oxford Nanopore sequencing libraries. In case of PacBio, the SMRT bells can be tagged on one or both side of the library fragments. In case consensus sequencing is desired, where the sequencing proceeds through the SMRT bells, the tag can be connected to the library fragment via a cleavable linker, and would be released prior to sequencing. Ion Torrent sequencing technology utilizes adapters very similar to Illumina, enabling on-bead clonal amplification of library fragments. These adapters can also be tagged with a quantifiable tag that can be used to easily quantify the molar concentration of the library fragments prior to clonal amplification, or prior to sequencing.

1. Preparing RNA for Amplification

The methods and compositions can be used for samples comprising single-stranded nucleic acids, in particular, RNA. In one embodiment, a cDNA library is produced from RNA in which molecules of first strand synthesis bear sequencing-platform specific sequences necessary and/or sufficient for sequencing on the sequencing platform. It will be understood that the original template can be DNA taken from any source, rather than RNA.

Figure 2:
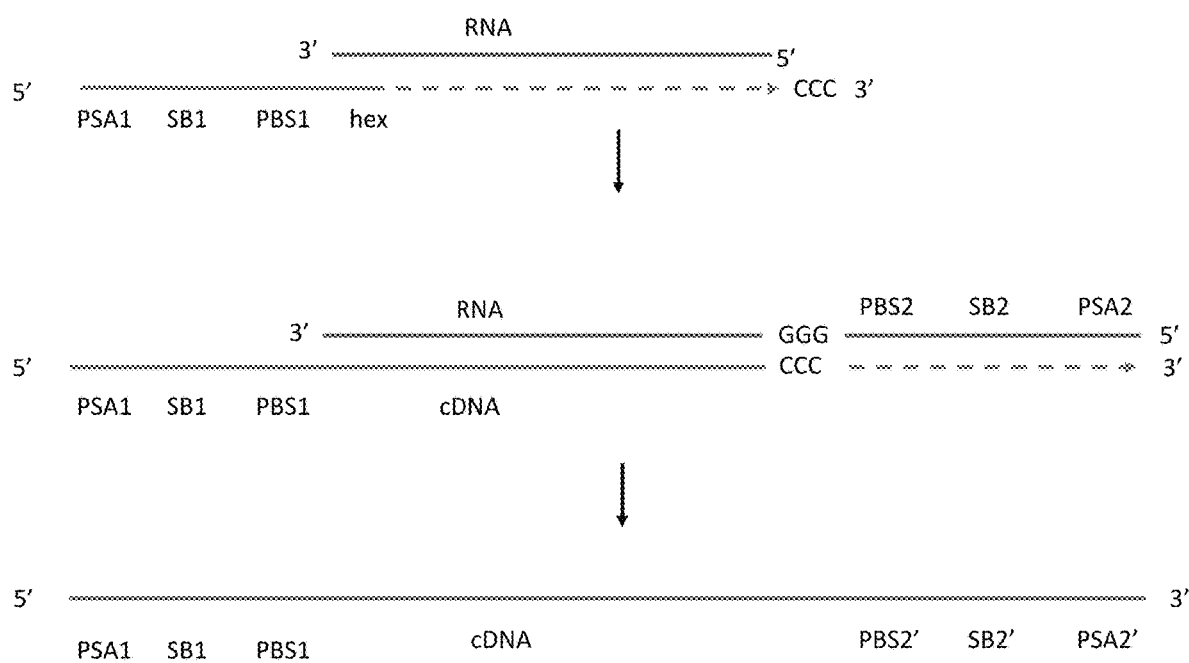
FIG. 2 shows an exemplary method of producing a first strand adapter-tagged cDNA molecule for primer-limited amplification.

Referring to FIG. 2, a sample comprising RNA molecules is provided. A first or forward primer/adapter is provided comprising a sequence for binding to an RNA molecule, for example, a degenerate hexamer sequence (hex). In certain embodiments, the primer further includes sequencing platform-specific sequences. In this example, platform-specific sequences are designated PSA1 and PSA2. For example, in the case of Illumina sequencers, these sequences may have the P5 and P7 sequences. Typically, adapters will also comprise a sample barcode (designated in FIG. 2 as ("SB1" and "SB2")). In the example of FIG. 2, the adapter/primers also bear primer binding sites 1 and 2. In Illumina sequencers, these sites may be used as sequencing primer binding sites.

The primer/adapter is hybridized to the RNA. Using a reverse transcriptase, such as Murine Maloney leukemia virus reverse transcriptase, the primer/adapter is extended, producing a cDNA strand having, at the 3' end, a poly C tail. A second adapter/primer is added to function as a further template. In this example, the second adapter/primer comprises, at the 3' end, a poly G tail adapted for hybridizing with the poly C tail. In certain embodiments the second adapter/primer also comprises sequencing platform-specific sequences and/or sample barcode sequences. The polymerase further extends the cDNA, producing a first strand adapter-tagged cDNA molecule comprising a cDNA insert flanked by adapter sequences. In the example of FIG. 2, the adapter sequences include platform-specific adapter sequences PSA1 and PSA2' (a template for PSA2 on complementary strand), sample barcodes SB1 and SB2' (a template for sample barcode SB2 on complementary strand), and secondary primer binding sites PB S1 and PBS2' (a template for PBS2 primer binding site on complementary strand).

The product of this reaction is adapter-tagged cDNA molecules.

2. Amplification of Adapter-Tagged Nucleic Acids

Adapter-tagged polynucleotides can be amplified in a plurality or rounds of primer extension, for example, PCR. At least one adapter-tag can comprise a sample nucleotide barcode, one or more primer binding sites and, optionally, sequencing platform-specific sequences for engaging amplified polynucleotides to a sequencing platform.

Amplification of adapter-tagged polynucleotides in each sample proceeds by contacting the adapter-tagged polynucleotides with primers. The primers are present in fixed molar amount, so that the final molar amount of amplified polynucleotide is determined by the molar amount of the primers.

In certain embodiments, forward and reverse primer binding sites are the same, and a single primer set comprising primers is used for amplification. In certain embodiments, amplification will proceed from forward and reverse primer binding sites having different sequences and flanking a region to be amplified. In this case, primers may be provided as primer pairs, a forward primer and a reverse primer, each member of the pair binding to one of the different binding sites. In such a situation the primers may be present in equal molar amount, or one primer may be present in known molar excess to the other.

Figure 3:
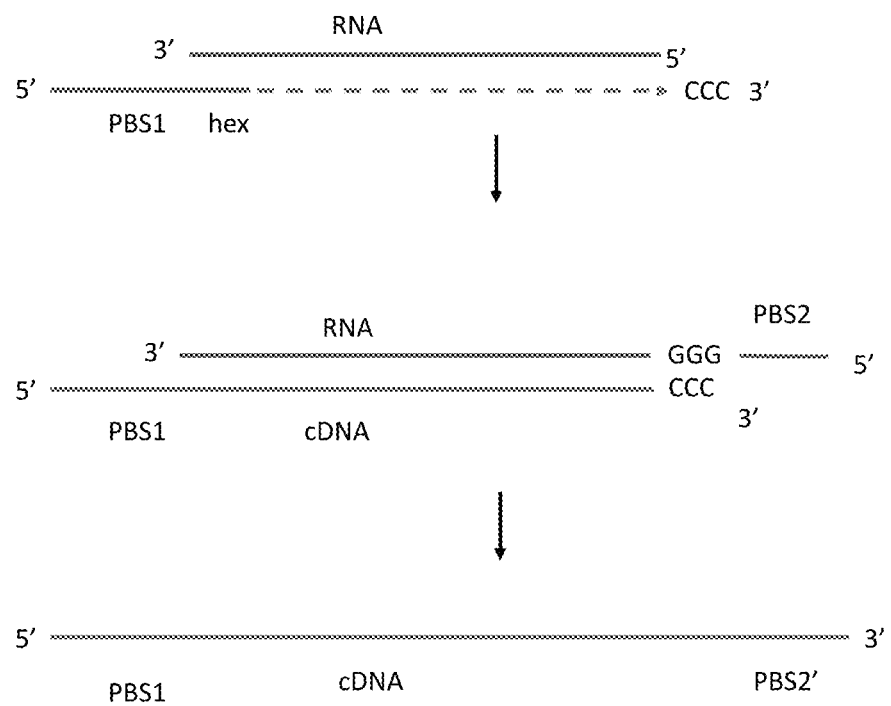
FIG. 3 shows an exemplary method of producing an adapter-tagged cDNA molecule from an RNA molecule. The adapters comprise primer binding sites (PBS1 and PBS2') which further function as amplification binding sites.

Referring to FIG. 3, according to one amplification strategy, adapter-tagged cDNA molecules are prepared from RNA by the method described above, except that adapter/primer molecules may bear only a set of forward and reverse primer binding sites (designated here as PBS1 and PBS2'). The result may be an adapter-tagged nucleic acid insert flanked by primer binding sequences.

Figure 4:
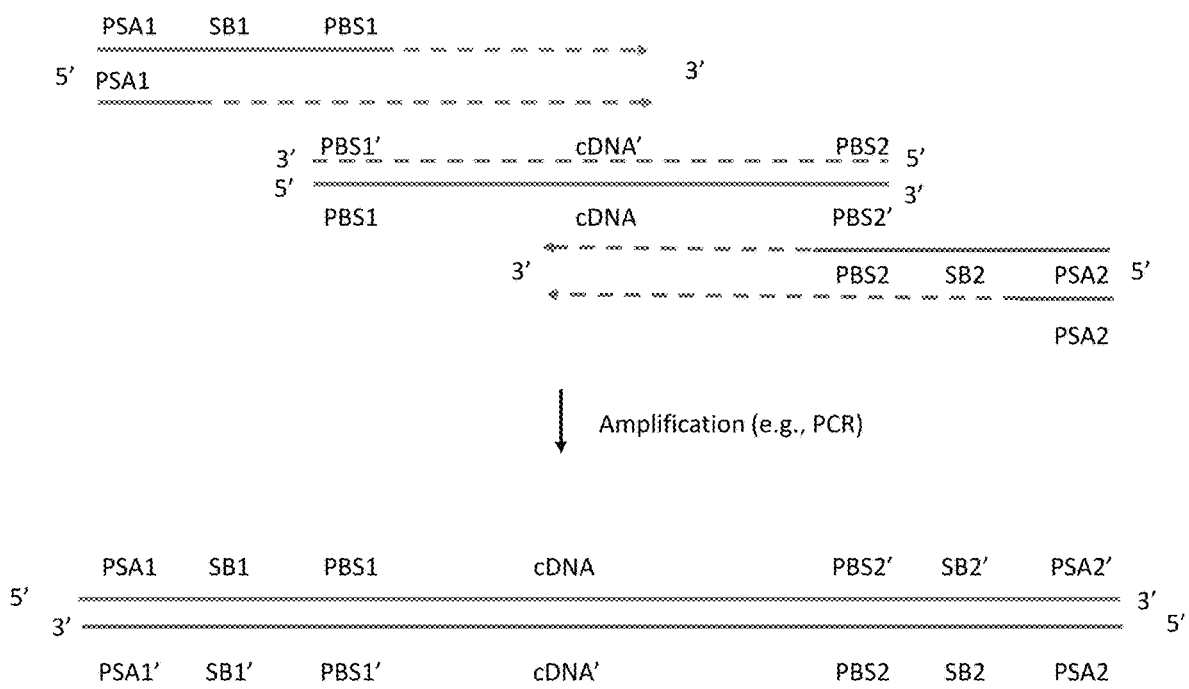
FIG. 4 shows an exemplary method of amplifying the adapter-tagged nucleic acid using two sets of forward and reverse primers, in a primer-limited amplification. A (phantom) complement of a cDNA strand is shown, for ease of understanding, as a dotted line. Not shown are products of first forward extension and first reversed extension.

Referring to FIG. 4, in this example, the adapter-tagged polynucleotide is a single stranded DNA molecule. (For purposes of clarity, the complement of this strand is also shown, however, a double stranded adaptor-tagged polynucleotide could be used in the same manner.) The adapter-tagged polynucleotide comprises a first primer binding site (PBS1), a target nucleic acid insert (in this case cDNA) and the complement of a second primer binding site (PBS2'). These molecules are contacted with two sets of primers.

Primers in a first set can comprise a forward primer comprising binding sequence (PBS1) that binds to first primer binding sites (PBS1') on the complement of the adapter-tagged polynucleotide. They can further comprise second primer binding sites which may function as platform-specific adapter sequences (PSA1). Primers in the first set may also comprise a sample barcode (SB1). Primers in the first set also include a reverse primer comprising a primer binding sequence (PBS2) that binds to second primer binding sites (PB S2') on the adapter-tagged polynucleotide. They can further comprise second primer binding sites which may function as platform-specific adapter sequences (PSA2). Primers in the first set may also comprise a second sample barcode (SB2).

Primers in a second set can comprise a sequence that binds to a primer binding site on the first set of primers. In the example depicted in FIG. 4, these primers bear primer binding sequences designated PSA1 and PSA2. These primers may not bear sequences contained in the first set of primers. For example, they may be shorter than the first set of primers. They may not bear sample barcodes. They may not bear sequences hybridizing to the primer binding sites on the initial adapter-tagged polynucleotide. The members of the second primer pair are added in a fixed molar amount, e.g., in equal molar amounts, or in a known ratio of molar amounts (one primer in excess).

In certain embodiments of the strategy, primer binding site 1 may also serve as a sequencing primer in a high throughput sequencing system, such as MiSeq, and/or the platform-specific adapter sequence may serve as a flow cell cluster site sequence, e.g., P5 and P7.

Upon amplification, the first set of primers convert adapter-tagged nucleic acid molecules into longer adapter-tagged nucleic acid molecules that comprise a sample barcode and the second primer binding site. In further rounds of amplification, primers of the second set will be used for strand extension for the longer adapter-tagged nucleic acid molecules. As a result, after sufficient rounds of amplification the population of amplified polynucleotides will reach a limit based on the molar amounts of the primers in the second pair of primers. If the primers are present in equal molar amounts, the final amplified molar amount of double-stranded nucleic acid will be equal to or substantially equal to the molar amount of each of the primers.

According to another amplification strategy, the original molecules are single- or double-stranded polynucleotides (e.g., end-repaired molecules). To these molecules are ligated adapters having, at least, primer binding sites. In the case of so-called "Y"-shaped adapters, the primer binding site on the free 5' end of the adapter is different than the primer binding site on the free 3' end of the adapter. Such molecules can be amplified with primer sets that hybridize to the primer binding sites and that may comprise platform-specific adapter sequences and, optionally, sample barcode sequences. The members of the primer set are added in fixed molar amounts, for example, in equal molar amounts, or in molar amounts related to each other in a known ratio. After sufficient rounds of amplification, amplified molecules are produced whose molar amount is determined by the molar amounts of primers added.

According to another amplification strategy, adapter-tagged nucleic acid molecules are amplified with a single primer set added in fixed molar amounts. After enough rounds of amplification to consume the primers, amplified nucleic acids comprising nucleic acid insert flanked by adapter sequences comprising primer binding sites and sample barcodes will be present in molar amounts determined by the molar amounts of primer added.

After primer extension and/or amplification, unincorporated primers, that is, primers that have not been used to support primer extension as part of strand synthesis, are typically removed from the sample; in the present methods, such a step may be unnecessary since all primer should be incorporated. However, if desired, potential unincorporated primers can be separated from the nucleic acid library by, for example, size selection or by hybridization to some complementary probes attached to a solid support.

C. Nucleic Acid Libraries

Using the methods and compositions described herein, it is possible to produce nucleic acid libraries.

In certain embodiments, the invention provides a set of a plurality of separate nucleic acid libraries, where each library contains amplified polynucleotides and where the molar amount of polynucleotides in each library are the same or substantially the same, or are related as a known ratio to each other. Each library may be in a separate container. The amplified polynucleotides may contain non-natural sequences, e.g., barcodes, primer sites, sequencing platform-specific sequences, and the like.

In certain embodiments the invention provides a pooled nucleic acid library including amplified nucleic acids from a plurality of different samples, where the nucleic acids from each sample are present in equal or substantially equal molar amounts, or in molar amounts that are known ratios of each other, and where the nucleic acids do not include a label. Nucleic acids from each sample may also incorporate a barcode that is different for each different sample.

D. Quantifying Amounts of Nucleic Acids in Each of a Plurality of Samples and Preparing Normalized and Normalized, Pooled Libraries Nucleic acid molecules in nucleic acid libraries so produced can be quantified based on the molar amounts of primers used in amplification. The molar amount of amplified nucleic acids in one library can be related to the molar amount of amplified nucleic acid in another library based on the molar amounts of primer used to produce each library. For example, if equal molar amounts of primer are used to produce amplified nucleic acids in each library, then the final molar amount of amplified nucleic acid in each library will be equal or substantially equal.

It will be appreciated that the precise molar amount of primer used to produce each library need not be known in order to produce libraries of amplified nucleic acids that are present in the same molar amount in each library, or in molar amounts related to each other in a known ratio. For example, if all samples used to produce nucleic acid libraries are tagged with adapters with the same primer binding sequences, a master pool of primers specific for the primer binding sequences may be prepared, and known volumes of the pool added to each sample. If equal volumes are added, equal molar amounts of primer are used and equal, or substantial equal, final molar amounts of amplified nucleic acid will be produced in each sample. If different volumes are used, the final molar amounts of amplified nucleic in the samples will be related according to the volumes of primers used in the samples.

Generally, no labeling or measurements of label or other properties of the nucleic acids is needed to quantify the final molar amount of nucleic acid in separate amplified libraries or in pooled libraries, since the final molar amount is directly related to the molar amount of primer used to produce the amplified nucleic acids. In certain embodiments, quantitation does not comprise providing an intercalating dye to nucleic acids and measuring an amount of dye intercalated. In certain embodiments, quantitation does not comprise providing labeled probes that hybridize to nucleic acid molecules and measuring an amount of probe hybridized to the nucleic acids.

E. Production of Libraries with Adjusted/Normalized Amounts of Polynucleotides

Using these methods, the relative molar amount of amplified nucleic acids in a sample can be controlled; in certain embodiments, the absolute molar amount of amplified nucleic acids in a sample is known. A plurality of libraries can have known amounts or concentrations of nucleic acid, and/or have amounts of nucleic acid in known molar ratios. These libraries can be used to produce pooled libraries.

In one embodiment, individual amplified nucleic acid libraries are produced by, for example, amplifying nucleic acids with fixed molar amounts of primers. In some cases, the molar amount of primer will be the same for all individual libraries. Then, portions of each amplified library can be combined into a pool. The molar amounts of primers used to produce each library, together with the portion of each library added to the pool, determines the relative molar amount of each library's nucleic acids in the final pool. For example, if equal molar amounts of primer are used in amplification to produce each library, and if 50% of each library is pooled with others to produce a pooled library, then nucleic acids from each individual library will be present in the pooled library in equal or substantially equal molar amounts (and, since there is only one volume for the pooled library, as equimolar or substantially equimolar concentrations). It will be appreciated that by manipulating one or both of molar amount of primer and portion of sample added to final pool, virtually any desired ratio of molar amounts of nucleic acids from the various libraries may be produced in the final pooled library. If the absolute molar amount of primers used to produce one or more individual amplified libraries is known, then the absolute molar amount of nucleic acid from those libraries in the pooled sample can be calculated.

In subsequent steps as described herein, nucleic acid libraries in which amounts of nucleic acid have been determined, or pooled libraries in which molar amounts of nucleic acids from individual samples are known, or are related in known molar ratios, can now be sequenced. Sequencing can proceed, for example, by high throughput sequencing.

F. Sequencing Libraries

Sequencing nucleic acid libraries produces sequence reads of the polynucleotides sequenced. Because nucleic acids in each nucleic acid library can bear a sample barcode sequence reads can be sorted into bins based on the original library from which they are sourced. Sequence reads from individual libraries can be subject to further analysis. In one embodiment, redundant sequences can be collapsed into an original sequence, e.g., a nucleotide by nucleotide. Raw sequence reads or collapsed reads may be referred to herein as "sequenced nucleic acids". Sequenced nucleic acids in any library can be analyzed to determine quantities of target sequences in the sample. For example, if the library comprises sequences of a microbiome, sequenced nucleic acids can be analyzed to determine species present in the sample and amount of each species. As another example, if the library comprises sequences of a transcriptome, sequenced nucleic acids can be analyzed to determine mRNAs present in the sample and amount of each mRNA.

There are many bioinformatics methods that convert raw sequences into secondary data. For example: Taxonomy classification uses databases with unique sequences belonging to different organisms. Once a sequence is matched to the database, the presence of a specific organism can be detected. By counting the sequences used to identify each organism, their relative abundances can also be measured. Functional assignments can also be made from the sequence reads. A database that correlates sequences to functions is used to convert sequencing reads into biochemical functions.

Figure 5:
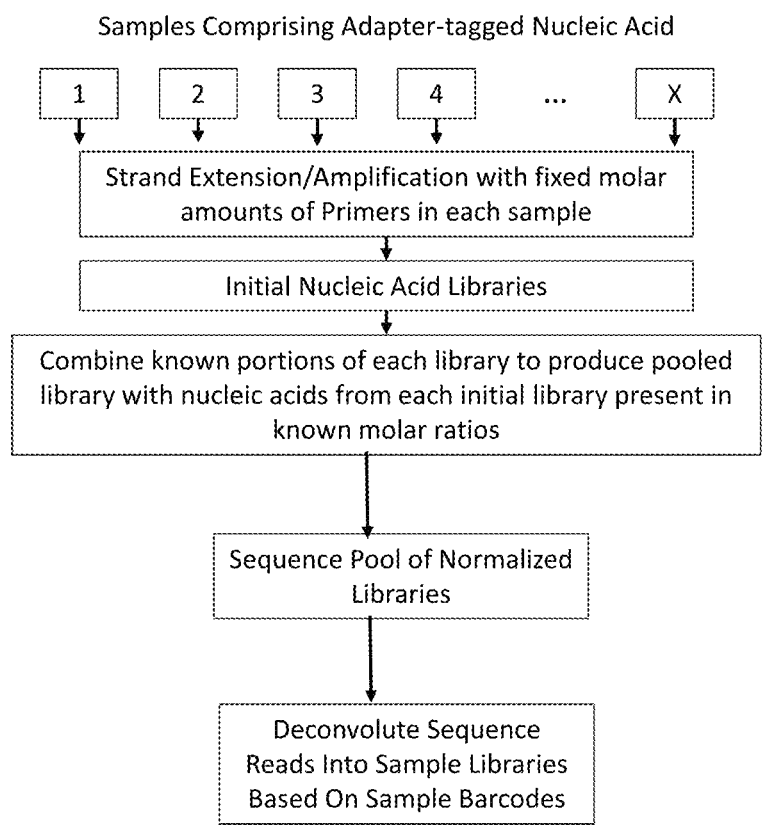
FIG. 5 shows an exemplary protocol for generating sequence reads from a pool of normalized nucleic acid libraries produced by primer-limited amplification.

FIG. 5 shows one exemplary protocol for amplification followed by sequencing.

G. Kits

Also provided herein are kits. Kits can comprise adapters and/or primers as disclosed herein. Kits can comprise reagents for performing biochemical reactions, such as reagents for primer extension and/or for amplification, such as PCR. Such reagents can include any of polymerases, reverse transcriptases, nucleotides and buffers, and other reagents and substances necessary or useful in a particular amplification technique. Kits can comprise containers for containing compositions of matter. Kits can comprise containers comprising the aforementioned containers. Kits also can comprise instructions for use, e.g., printed instructions.

In certain embodiments, kits comprise sets of primers as described herein, where each set of primers is contained in a separate container or containers, for example, a set of first and second primers, such as forward and reverse primers. Each container has a fixed molar amount of primer which is in a known ratio to the molar amounts of primer in other containers, e.g., an equal molar amount or substantially equal molar amount. The absolute molar amount of primer in one or more containers may be known. Primers from the separate containers may be used in primer extension amplification in separate samples, to produce amplified nucleic acids in the samples. The first and second primers may have the same or different polynucleotide sequences. The kit can further include adapter sequences, which may include primer binding sites, barcodes, sequencing platform-specific sequences, or a combination thereof. The kit may further include reagents for performing nucleic acid amplification, for example, reagents for performing PCR, LAMP, RT-LAMP, SDA, HDA, or TMA.

A kit may also contain a single container with pooled primers, which are adapted for binding to universal primer binding sites provided by adapters, where a volume of the pooled primers added to each of separate nucleic acid samples determines the final molar ratio of amplified nucleic acids in the samples after amplification. The absolute molar amount of primer in a volume of the pooled primer may be known. Adapters may also be packaged in the, or in a separate kit. A single container may also contain an adapter, aliquots of which may be used in individual samples to provide adapter-modified nucleic acids ready for amplification; however, in general, adapter may have barcode sequences to distinguish separate nucleic acid samples, and adapters with different barcodes are packaged in different containers. Adapters may include primer binding sites (e.g., the same primer binding site will be present in each separate sample after incorporation of adapters into nucleic acids in the sample), barcodes, sequencing platform-specific sequences, or a combination thereof. The kit may further include reagents for performing nucleic acid amplification, for example, reagents for performing PCR, LAMP, RT-LAMP, SDA, HDA, or TMA.

V. Methods and Compositions for Amplification of Nucleic Acids with Detectable Labels Also provided herein are methods of determining molar concentration or amounts of nucleic acid molecules in a sample. Further provided herein are methods of preparing normalized nucleic acid libraries comprising predetermined molar amounts of nucleic acid, which amounts have been determined, e.g., by methods provided herein. Also provided herein are pooled, nucleic acid libraries comprising normalized amounts of nucleic acid derived from each of a plurality of different samples. That is, each library contributes a normalized amount of nucleic acid molecules to the pooled library. In certain embodiments, the normalized libraries have equal molar amounts of nucleic acid (that is, number of molecules as opposed to mass of nucleic acid).

The molar concentration or quantity of adapter-tagged polynucleotides in the sample can be determined. Normalized, pooled nucleic acid libraries can be prepared and sequenced directly, e.g., without further amplification or with limited amplification, e.g., fewer than any of a one, 2, 5, or 10, rounds of amplification.

Methods of determining amounts of nucleic acid in a sample comprise performing one or a plurality of primer extension reactions using primers, at least a portion of which comprise a detectable label, and detecting label incorporated into synthesized molecules. In certain embodiments, nucleic acids are quantified after one or two rounds of primer extension using labeled primers, e.g., after first and/or second strand synthesis from a template molecule, such as RNA. In other embodiments, nucleic acids are quantified after a plurality of rounds of amplification, e.g., after a plurality of rounds of PCR, in which at least a portion of the primers used for amplification comprise a detectable label.

According to one method an amount of RNA in a sample is determined. The RNA can be subject to first strand synthesis (reverse transcription) to produce cDNA using first primers, at least a portion of which comprise a detectable label, such as a fluorescent tag. The amount of detectable label incorporated into the first strand synthesis product can be measured. The amount of nucleic acid in the sample is a function of signal produced by the detectable label. In certain embodiments, the primers used during first strand synthesis may comprise nucleotide sequences that are necessary and/or sufficient for sequencing on a specific sequencing platform. When performed on a plurality of different samples a pool of nucleic acid libraries can be produced in which the amounts of nucleic acids from each library are normalized with respect to each other based at least in part on the amounts of nucleic acid detected in each sample. The pooled sample can be used to populate a sequencing flow cell. Upon sequencing, quantities of nucleic acid sequences between samples can be compared directly to one another.

According to one method, nucleic acid in a sample is amplified, for example by a plurality of rounds of PCR, using primers bearing a detectable label. After amplification, the amount of amplified nucleic acid in the sample is measured as a function of incorporated detectable label. Pooled, normalized nucleic acid libraries can be prepared from a plurality of samples based on the amounts of nucleic acid in each sample as determined by the method provided herein.

Also provided here are normalized DNA libraries and pooled, normalized DNA libraries in which at least some of the amplified molecules bear the detectable label.

A. Preparation of Nucleic Acid Libraries Comprising Polynucleotides Comprising a Label.

Preparation of nucleic acid libraries comprising polynucleotides comprising a detectable label typically involves creation of adapter tagged polynucleotides. Adapters can be provided by hybridization of primers comprising adapter sequences to target molecules, followed by primer extension, or by ligation of the adapters to nucleic acids in a sample. Primer extension is typically used with single-stranded target nucleic acids. Double stranded nucleic acids can be tagged through primer extension or ligation. Primer extension can be useful to amplify target sequences in long nucleic acid molecules. Ligation of adapter is particularly useful for tagging short, double stranded nucleic acid molecules, such as cell-free DNA. Detectable label is typically introduced during a primer extension step, which can be performed on a target molecule or during amplification of double stranded molecules.

Methods disclosed herein comprise performing one or a plurality of primer extension reactions on nucleic acid molecules in a sample, either original, untagged molecules, or adapter-tagged molecules. Primer extension is performed using polynucleotide primers, at least a portion of which bear a detectable label. Primer extension can use a single set of primers or a plurality (e.g., two) primer sets. In the case of a single primer set, all or substantially all of the primers can bear a label or a portion or a fraction (fewer than 100%) can bear a label. In the case of multiple primer sets, all of the primers can bear a label. More typically, a portion (fewer than all) primers can bear a detectable label. In such embodiments, a first set of primers can comprise primers bearing a label while primers in a second set of primers do not bear a label. For example, all or substantially all primers in a first set can bear a label while primers in a second set bear no label. In another embodiment, a portion of the primers in each a plurality of primer sets bear a label.

The ratio of primer or adapter bearing a detectable label to those not bearing a detectable label can range from 1:100 to 100:1. More typically, the ratio will be between about 10:1 to 1:10, about 1:5 to 5:1, about 1:3 to 3:1, about 1:2 to 2:1 or about 1:1. In certain embodiments all of the primers (100%) bear a detectable label. These ratios apply where two sets of primers are used, each binding to a different primer binding site, and primers in one set all bear a label, while no primers in the other set bear a label.

Depending on the primer strategy used and percent of primers bearing a detectable label, the collection of amplified molecules can include those bearing no label, those bearing a single label and those bearing two labels. The percentage of amplified molecules falling in each group depends on the ratio of labeled two unlabeled primers used. Where the percentage of labeled primers is "p", the percentage of amplified molecules bearing to labels will be p2 P squared. The percentage of amplified molecules bearing one label will be 2*p*(1−p). The percentage of amplified molecules bearing no label will be (1−p)2.

The product of primer extension reactions is a nucleic acid library, in which at least a portion of the polynucleotides in the library incorporate the detectable label. The amount of detectable label in the library can be measured. This provides an indication of the amount of nucleic acid in a single library, or the relative amounts of nucleic acids in a plurality of libraries.

In order to quantify nucleic acids in a sample or a library, detectable labels are incorporated into nucleic acids in a stoichiometric manner during primer extension or amplification. The amount of detectable label incorporated provides a measure of the molar concentration of nucleic acids in the sample.

In certain embodiments incorporated detectable label can be measured after a single primer extension reaction using extension primers bearing a detectable label. In other embodiments detectable label can be measured after a plurality of rounds of primer extension, e.g., after a plurality of rounds of amplification for example by PCR.

In certain embodiments of the disclosed methods, adapter-tagged molecules comprise sequencing platform-specific sequences compatible with a particular sequencing platform. For example, in the case of Illumina MiSeq devices, platform-specific sequences can include a sequencing primer binding site and a flow cell cluster primer binding site. Preparation of tagged libraries whose molar concentration can be easily determined is not limited to any one technology. For example, this method can be used to prepare PacBio, Ion Torrent, and Oxford Nanopore sequencing libraries. In case of PacBio, the SMRT bells can be tagged on one or both side of the library fragments. In case consensus sequencing is desired, where the sequencing proceeds through the SMRT bells, the tag can be connected to the library fragment via a cleavable linker, and would be released prior to sequencing. Ion Torrent sequencing technology utilizes adapters very similar to Illumina, enabling on-bead clonal amplification of library fragments. These adapters can also be tagged with a quantifiable tag that can be used to easily quantify the molar concentration of the library fragments prior to clonal amplification, or prior to sequencing.

B. Libraries for Quantification and Sequencing after One Primer Extension Reaction In one embodiment, incorporated detectable label is measured after one, or a few primer extension reactions. The method can be used for samples comprising single-stranded nucleic acids, in particular, RNA. In one embodiment of the strategy, a cDNA library is produced from RNA in which molecules of first strand synthesis bear sequencing-platform specific sequences necessary and/or sufficient for sequencing on the sequencing platform. At least a portion of these molecules incorporated detectable label. It will be understood that the original template can be DNA taken from any source, rather than RNA.

Figure 6:
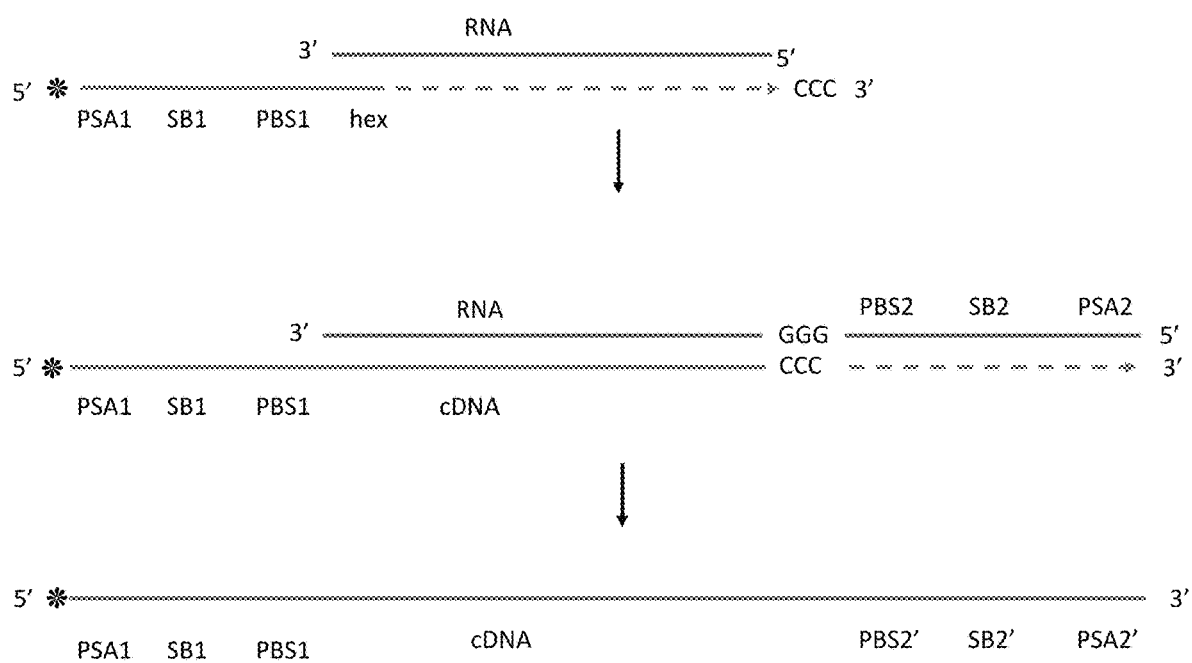
FIG. 6 shows an exemplary method of producing a first strand adapter-tagged cDNA molecule comprising a detectable label.

Referring to FIG. 6, a sample comprising RNA molecules is provided. A first or forward primer/adapter is provided comprising a sequence for binding to an RNA molecule, for example, a degenerate hexamer sequence (hex). In certain embodiments, the primer further includes sequencing platform-specific sequences. In this example, platform-specific sequences are designated PBS1 and PBS2. For example, in the case of Illumina sequencers, these sequences may have the P5 and P7 sequences. Typically, adapters will also comprise a sample barcode (designated in FIG. 2 as ("SB1" and "SB2")). In the example of FIG. 6, the adapter/primers also bear primer binding sites 1 and 2. In Illumina sequencers, these sites may be used as sequencing primer binding sites. Some or all of the first primer/adapter molecules comprise a detectable label (*).

The primer/adapter is hybridized to the RNA. Using a reverse transcriptase, such as Murine Maloney leukemia virus reverse transcriptase, the primer/adapter is extended, producing a cDNA strand having, at the 3' end, a poly C tail. A second adapter/primer is added to function as a further template. In this example, the second adapter/primer comprises, at the 3' end, a poly G tail adapted for hybridizing with the poly C tail. In certain embodiments the second adapter/primer also comprises sequencing platform-specific sequences and/or sample barcode sequences. The polymerase further extends the cDNA, producing a first strand adapter-tagged cDNA molecule comprising a cDNA insert flanked by adapter sequences. In the example of FIG. 6, the adapter sequences include platform-specific adapter sequences PSA1 and PSA2', sample barcodes SB1 and SB2', and secondary primer binding sites PBS1 and PB S2'. at least one primer binding site. Typically, library molecules are separated from unincorporated primers to remove excess label.

The product of this reaction is adapter-tagged cDNA molecules, at least some of which bear a detectable label.

In certain embodiments the nucleic acid libraries can be sequenced without performing subsequent amplification reactions, with no more than 2, 3 or 4 rounds of amplification or with more than 2, 4, 8 or 16 rounds of amplification.

C. Libraries for Quantification and Sequencing after Amplification of Adapter-Tagged Nucleic Acids Detectable label can be incorporated into adapter-tagged polynucleotides by one or a plurality or rounds of primer extension, for example, amplification, for example, PCR. At least one adapter-tag can comprise a sample nucleotide barcode, one or more primer binding sites and, optionally, sequencing platform-specific sequences for engaging amplified polynucleotides to the sequencing platform.

Amplification of adapter-tagged polynucleotides in each sample proceeds by contacting the adapter-tagged polynucleotides with primers. At least a portion of the primers bear a detectable label.

In certain embodiments, forward and reverse primer binding sites are the same, and a single primer set comprising labeled primers is used for amplification and incorporation of detectable label. In certain embodiments, amplification will proceed from forward and reverse primer binding sites having different sequences and flanking a region to be amplified. In this case, primers may be provided as primer pairs, a forward primer and a reverse primer, each member of the pair binding to one of the different binding sites. In such a situation one or both or none of the members of the pair may bear a detectable label.

Referring to FIG. 3, according to one amplification strategy, adapter-tagged cDNA molecules are prepared from RNA by the method described above, with the following differences. First, the primer/adapters used to first incorporate adapter sequences into molecules may not bear a detectable label. Second, the adapter/primer molecules may bear only a set of forward and reverse primer binding sites (designated here as PBS1 and PBS2'). The result may be an adapter-tagged nucleic acid insert flanked by primer binding sequences.

Figure 7:
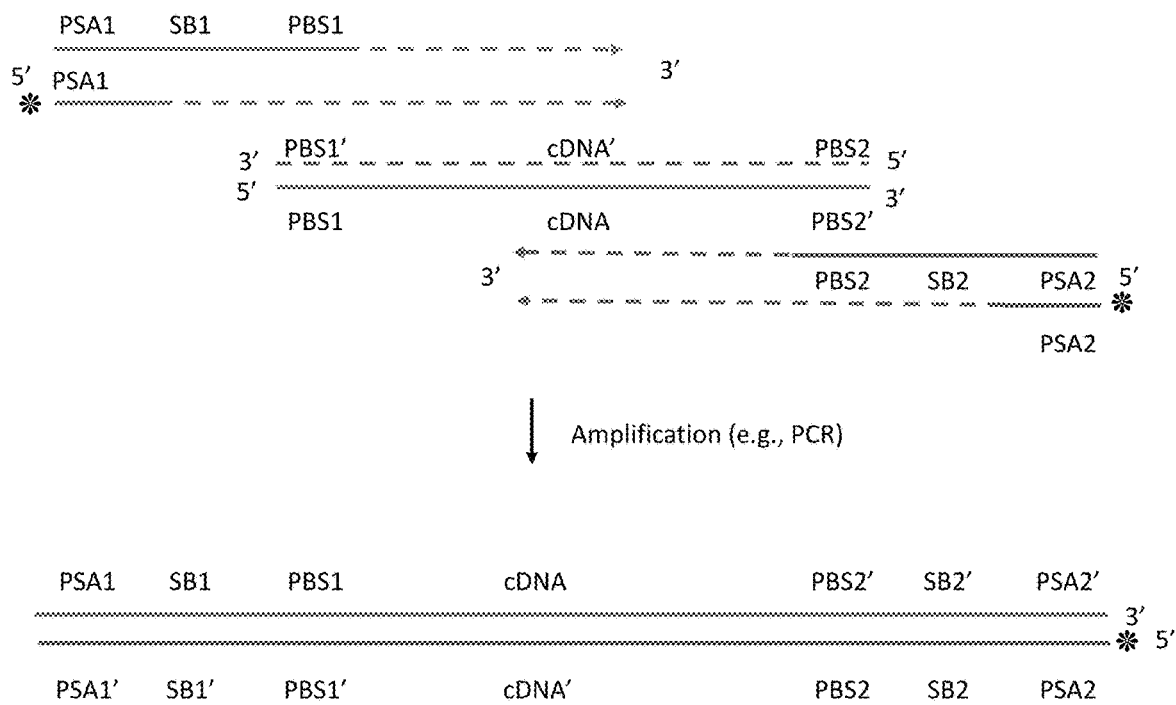
FIG. 7 shows an exemplary method of amplifying the adapter-tagged nucleic acid using two sets of forward and reverse primers, in a amplification with normalization by labeling. A (phantom) complement of a cDNA strand is shown, for ease of understanding, as a dotted line. Not shown are products of first forward extension and first reversed extension.
Figure 8:
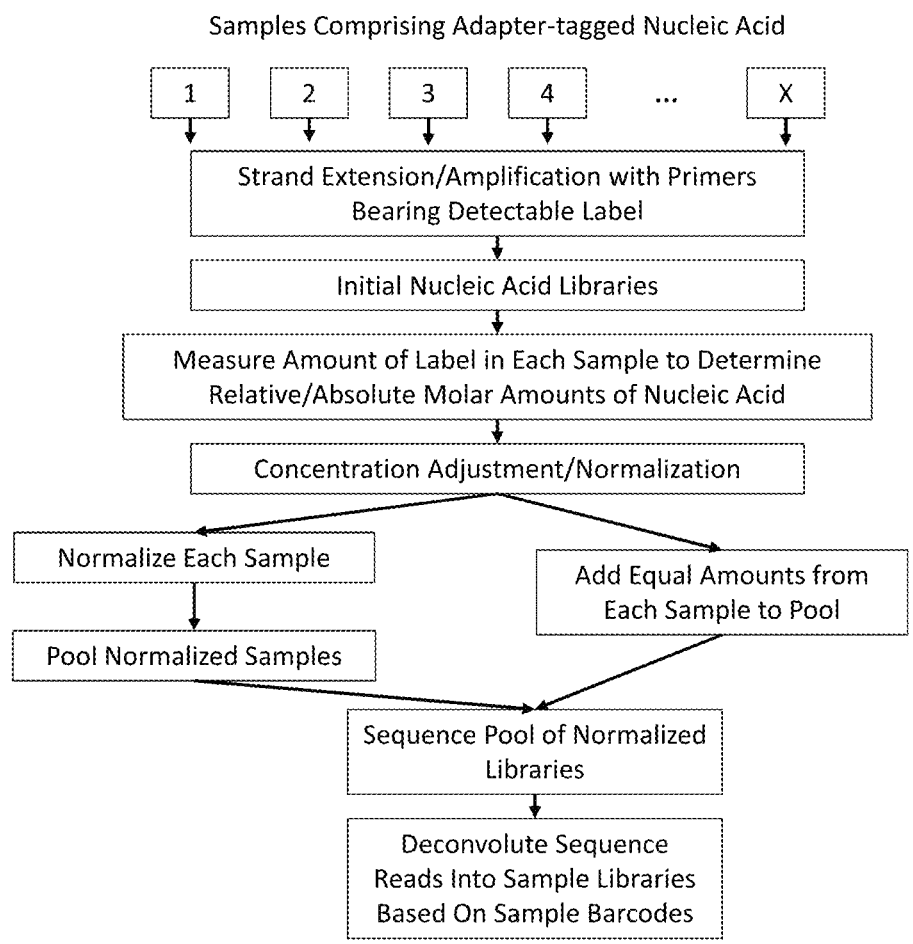
FIG. 8 shows an exemplary protocol for generating sequence reads from a pool of normalized nucleic acid libraries produced by labeling.

Referring to FIG. 7, in this example, the adapter-tagged polynucleotide is a single stranded DNA molecule. (For purposes of clarity, the complement of this strand is also shown, however, a double stranded adaptor-tagged polynucleotide could be used in the same manner.) The adapter-tagged polynucleotide comprises a first primer binding site (PBS1), a target nucleic acid insert (in this case cDNA) and a second primer binding site (PBS2'). These molecules are contacted with two sets of primers.

Primers in a first set can comprise a forward primer comprising binding sequence (PBS1) that binds to first primer binding sites (PBS1') on the complement of the adapter-tagged polynucleotide. They can further comprise second primer binding sites which may function as platform-specific adapter sequences (PSA1). Primers in the first set may also comprise a sample barcode (SB1). Primers in the first set also include a reverse primer comprising a primer binding sequence (PBS2) that binds to second primer binding sites (PB S2') on the adapter-tagged polynucleotide. They can further comprise second primer binding sites which may function as platform-specific adapter sequences (PSA2). Primers in the first set may also comprise a second sample barcode (SB2). In this example, primers in the first set are free of a detectable label. Alternatively, a portion of them may comprise a detectable label.

Primers in a second set can comprise a sequence that binds to a primer binding site on the first set of primers. In the example depicted in FIG. 7, these primers bear primer binding sequences designated PSA1 and PSA2. These primers may not bear sequences contained in the first set of primers. For example, they may be shorter than the first set of primers. They may not bear sample barcodes. They may not bear sequences hybridizing to the primer binding sites on the initial adapter-tagged polynucleotide. Typically, a portion, or all, of the primers in the second set comprise a detectable label (*). In certain embodiments, only one of the members of the pair of second primers bears the detectable label. In the embodiment shown here, both members of the pair of second primers bears the detectable label.

In certain embodiments of the strategy, primer binding site 1 may also serve as a sequencing primer in a high throughput sequencing system, such as MiSeq, and/or the platform-specific adapter sequence may serve as a flow cell cluster site sequence, e.g., P5 and P7.

Upon amplification, the first set of primers convert adapter-tagged nucleic acid molecules into longer adapter-tagged nucleic acid molecules that comprise a sample barcode and the second primer binding site. In further rounds of amplification, primers of the second set comprising the detectable label will be used for strand extension for at least some of the longer adapter-tagged nucleic acid molecules. As a result, after several rounds of amplification the population of amplified polynucleotides will include a first sub-population bearing the detectable label and a second sub-population free of the detectable label. If the ratio of second primers to first primers is high, and the second primers, but not the first bear a detectable label, a majority or substantially all of the amplified molecules will bear a detectable label.

According to another amplification strategy, the original molecules are single- or double-stranded polynucleotides (e.g., end-repaired molecules). To these molecules are ligated to adapters having, at least, primer binding sites. In the case of so-called "Y"-shaped adapters, the primer binding site on the free 5' end of the adapter is different than the primer binding site on the free 3' end of the adapter. Such molecules can be amplified with primer sets that hybridize to the primer binding sites and that comprise platform-specific adapter sequences and, optionally, sample barcode sequences. At least a portion of the primers in this amplification set are detectably labeled. After several rounds of amplification, amplified molecules, at least some of which bear a detectable label, are produced.

According to another amplification strategy, adapter-tagged nucleic acid molecules are amplified with a single primer set in which a fraction, but not all, of the primers in the set bear a detectable label. After several rounds of amplification amplified nucleic acids comprise nucleic acid insert flanked by adapter sequences comprising primer binding sites and sample barcodes. In this population a percentage of molecules will bear no detectable labels a percentage of molecules will bear one detectable label (on either side of the molecule) and a certain percentage of molecules will bear to detectable labels, one on each strand.

After primer extension and/or amplification, unincorporated primers, that is, primers that have not been used to support primer extension as part of strand synthesis, are typically removed from the sample. Unincorporated primers can be separated from the nucleic acid library by, for example, size selection or by hybridization to some complementary probes attached to a solid support.

D. Quantifying Amounts of Nucleic Acids in Each of a Plurality of Samples and Preparing Normalized and Normalized, Pooled Libraries Nucleic acid molecules in nucleic acid libraries so produced can be quantified by measuring detectable label incorporated into library molecules. Determining amounts can be relative or absolute. Quantifying relative amounts can involve using measured signal to compare with measured signal from other samples. Absolute measurement can involve determining molar amounts or concentrations of nucleic acids in a sample, for example, based on a standard curve.

Because label is introduced into nucleic acids in a stoichiometric manner, relative amounts of amplified nucleic acids between samples can be compared. If the detectable label is, for example, a fluorescent label, fluorescence from each sample can be measured. Absolute amounts of nucleic acid in a sample can be determined, for example, through the use of a standard curve based on control samples. Alternatively, relative amounts of nucleic acids between samples can be determined based on relative quantity of detectable signal measured in each sample.

Colorimetry: Chemical reactions can generate products that produce specific color. At the molecular level, the absorption spectrum of the product is distinctly different from that of the substrate(s). For example, if the detectable label is an enzyme that generates a product with absorption at a different wavelength than any of the reactants, then the detectable label can be indirectly quantified by the amount colorimetric product produced.

In case primers with fluorescent labels are used to generate cDNA or DNA libraries, the finished libraries will carry the label. In parallel, calibration standards could be prepared using the same method and reagents as the samples. The standards could be prepared in large amounts and their molar concentration determined using another quantification method (e.g. UV absorbance or intercalating dyes) and known molecular weight (MW). The MW can be computed if the standards have a known length, or can be measured using an appropriate analytical method, such as capillary electrophoresis (e.g. Fragment Analyzer instrument). The standards could then be used to quantify libraries from samples using their fluorescent labels.

In certain embodiments, quantitation does not comprise providing an intercalating dye to nucleic acids and measuring an amount of dye intercalated. In certain embodiments, quantitation does not comprise providing labeled probes that hybridize to nucleic acid molecules and measuring an amount of probe hybridized to the nucleic acids.

E. Production of Libraries with Adjusted/Normalized Amounts of Polynucleotides

Using these measurements, concentration of nucleic acids in a sample can be adjusted to a predetermined or normalized amount. A plurality of libraries can have normalized amounts or concentrations of nucleic acid. Normalized libraries can be used in pooled, normalized libraries.

In one embodiment, individual normalized libraries are produced by, for example, diluting different samples to produce the desired molarity for each sample. In some cases, the molarity will be the same for all samples. Then, the same volumes of each normalized sample can be combined into a pool.

In another embodiment, volumes of different samples, each volume containing the same amount of nucleic acid, are removed from each sample and combined into same volume second samples.

In another embodiment, volumes of different samples, each volume containing the same amount of nucleic acid, are combined into a common pool to produce a pool of normalized libraries.

In subsequent steps as described herein, nucleic acid libraries in which amounts of nucleic acid have been determined, or pooled libraries can now be sequenced. Sequencing can proceed, for example, by high throughput sequencing.

F. Sequencing Pooled Libraries

Sequencing nucleic acid libraries produces sequence reads of the polynucleotides sequenced. Because nucleic acids in each nucleic acid library bear a sample barcode sequence reads can be sorted into bins based on the original library from which they are sourced. Sequence reads from individual libraries can be subject to further analysis. In one embodiment, redundant sequences can be collapsed into an original sequence, e.g., a nucleotide by nucleotide. Raw sequence reads or collapsed reads may be referred to herein as "sequenced nucleic acids". Sequenced nucleic acids in any library can be analyzed to determine quantities of target sequences in the sample. For example, if the library comprises sequences of a microbiome, sequenced nucleic acids can be analyzed to determine species present in the sample and amount of each species.

There are many bioinformatics methods that convert raw sequences into secondary data. For example: Taxonomy classification uses databases with unique sequences belonging to different organisms. Once a sequence is matched to the database, the presence of a specific organism can be detected. By counting the sequences used to identify each organism, their relative abundances can also be measured. Functional assignments can also be made from the sequence reads. A database that correlates sequences to functions is used to convert sequencing reads into biochemical functions.

G. Kits

Also provided herein are kits. Kits can comprise adapters and/or primers as disclosed herein. Kits can comprise reagents for performing biochemical reactions, such as reagents for primer extension and/or for amplification, such as PCR. Such reagents can include any of polymerases, reverse transcriptases, nucleotides and buffers. Kits can comprise containers for containing compositions of matter. Kits can comprise containers comprising the aforementioned containers. Kits also can comprise instructions for use, e.g., printed instructions.

In some embodiments, kits comprise primers as described herein, in which a portion of the primer comprise a detectable label and a portion do not comprise a detectable label. The primers having a label can have the same sequences as those not having a label. In some embodiments, the kit can comprise first and second sets of primers/adapters. A first set can have sequences that binding to a target primer binding site on a target polynucleotide. A second set can comprise sequences that bind to primer binding sites on primers in the first set. In certain embodiments, only primers in the second set bear detectable labels.

The following examples are offered by way of illustration and not by way of limitation.

EXAMPLES

Example 1: Preparation of Libraries from RNA

A method of preparing an RNA library comprises:
a) providing a sample containing: (i) from about 5 μL to about 100 μL(e.g., about 20 μL to about 50 μL) and (ii) an RNA preservative [inhibits degradation of RNA];
b) optionally, disrupting cells in the sample;
c) isolating polynucleotides from the sample (e.g., on a silica surface) (optionally, at this stage, non-informative RNA, such rRNA and common host mRNA can be removed from the sample);
d) degrading DNA in the isolated polynucleotides (e.g., with a DNase) to produce an RNA-enriched sample;
e) converting RNA into cDNA that contains primer sites for forward and reverse primers
f) amplifying the cDNA of step e) using fixed molar amounts of forward and reverse primers, where the amounts are the same, through a sufficient number of amplification cycles to consume all of the first and second primer.

Example 2: Normalized Nucleic Acid Libraries By Primer-Limited Amplification

A plurality of different samples comprising RNA are provided; each sample is in a separate container. To obtain a pooled normalized library of amplified nucleic acids from the samples 1. Each of the plurality of samples is treated as in Example 1, where the fixed molar amount of primer used in each sample is the same, or is related in a known ratio. Each sample is treated to label the nucleic acid with a barcode, where the barcodes for each sample are different.

2. A portion of each sample is removed and pooled with portions from other samples. The relative molar amounts of nucleic acids from each sample in the pooled sample is determined by the fixed molar amount of primer used to amplify each sample, and by the relative portion of each sample added to the pooled sample.

Figure 9:
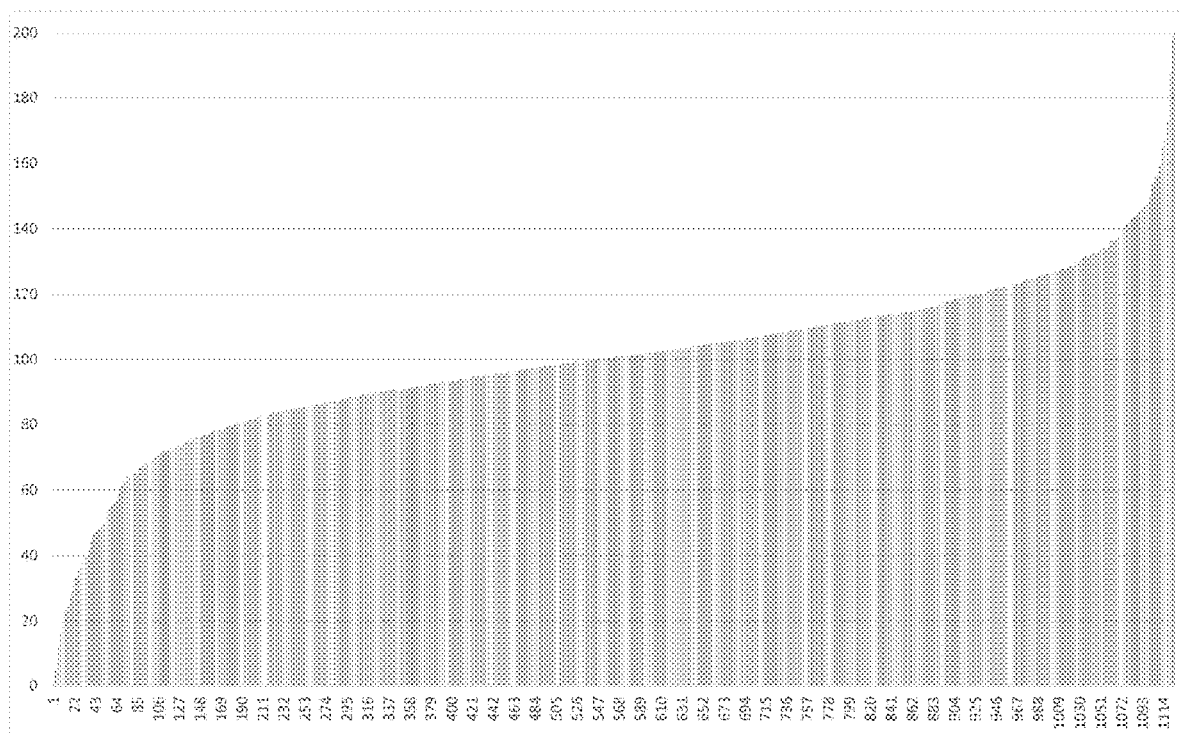
FIG. 9 shows the number of reads as a percentage of the mean for 1125 samples amplified according to the primer-limited methods described herein then read on an Illumina sequencer; see Example 3.

Example 3: Normalized Nucleic Acid Libraries with Sequencing 1125 samples containing nucleic acid (e.g., RNA) were provided and amplified according to the primer-limited methods described herein, then sequenced on an Illumina sequencer. The mean number of reads was 8,727,908. 1051 samples had a number of reads within 50% of the mean, representing 93.4% of the samples within the 50% cutoff. See FIG. 9. This represents far greater consistency than the current state of the art; see, e.g., Hosomichi et al., BMC Genomics 2014 15:645 (http://www.biomedcentral.com/1471-2164/15/645), in which ~50% of the samples were found to be within 50% of the mean.

Example 4: Normalized Libraries By Labeled Amplification

A sample comprising RNA is provided. To the sample is added a forward primer. The forward primer comprises a 3' backspace.

1. During library preparation amplification step, add fluorescent primers that amplify the cDNA fragments and incorporate fluorescence in them:
Option A: Use only fluorescently-labeled PCR primers that contain barcodes.
Option B: Combine non-fluorescent primers with barcodes and shorter fluorescent primers that do not contain the barcode. This way, the fluorescent primers are universal for all libraries. Fraction of total primers that are fluorescent can be anywhere between 0-100%, depending on the fluorescence yield of the fluorophore and the sensitivity of the fluorometer used to quantify the libraries.

2. Purify the libraries to remove any unincorporated fluorescent primers. This can be done with commercially available kits.

3. Quantify the molar concentration of each library using a fluorometer. Use quantity standards for this purpose. Molarity can be computed because the fluorophores are added in a fixed stoichiometric ratio to all libraries. Average library length does not affect the fluorescence signal.

4. (Optional) Cleave off the fluorescent tag if a cleavable linker was used.

5. Normalize the libraries as needed based on the molar concentration determined in step 3.

All publications and patent applications mentioned in this specification are herein incorporated by reference to the same extent as if each individual publication or patent application were specifically and individually indicated to be incorporated by reference.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A primer-limited method for processing and normalizing nucleic acids in a plurality of subsamples from a sample of a microbiome of a host wherein the sample comprises nucleic acids and/or cells comprising nucleic acids, wherein the nucleic acids are from one or more microorganisms in the microbiome, comprising:

(A) providing the plurality of subsamples derived from the sample of the microbiome of the host, wherein each subsample comprises a corresponding plurality of polynucleotides that comprise the nucleic acids or derived from the nucleic acids;

(B) performing, for each respective subsample in the plurality of subsamples, a plurality of rounds of polymerase chain reaction (PCR) on the corresponding plurality of polynucleotides, or derivatives thereof, using a corresponding one or more primers for a different target nucleic acid in the respective subsample, thereby obtaining amplified polynucleotides, wherein for the respective subsample:
2-50 rounds of PCR are performed,
each primer of the corresponding one or more primers is provided in a fixed molar amount,
each primer of the corresponding one or more primers is completely or substantially completely consumed in the 2-50 rounds of PCR for the respective subsample, and
a molar amount of the amplified polynucleotides for the respective subsample is determined by the fixed molar amount of each primer of the one or more primers in that subsample;
wherein the one or more primers and PCR are in solution; and (C) generating, after the amplifying, a pooled sample from the plurality of subsamples, wherein a relative molar amount of amplified polynucleotides from each subsample in the pooled sample is determined by (i) the fixed molar amount of primers used to amplify each subsample, and (ii) the relative portion of each subsample added to the pooled sample, and wherein the amplified polynucleotides are not washed or isolated from a solid support prior to pooling.

2. The method of claim 1 wherein the host is a human.

3. The method of claim 1 wherein the sample comprises a stool sample.

4. The method of claim 1 wherein the polynucleotides comprise RNA and the method further comprises producing cDNA from the RNA to provide cDNA derivatives of the RNA.

5. The method of claim 4 further comprising removing noninformative RNA before producing the cDNA.

6. The method of claim 1 wherein the plurality of subsamples comprise at least 10 subsamples.

7. The method of claim 1 wherein the method further comprises sequencing the amplified polynucleotides.

8. The method of claim 1 wherein 20-40 rounds of PCR are performed.

9. The method of claim 1 wherein 24-28 rounds of PCR are performed.

10. The method of claim 1 wherein one or more primers is provided in an amount between $7.5 \times 10^{-13}$ to $2 \times 10^{-12}$ mole.

11. The method of claim 1 wherein one or more primers is provided in an amount between $1 \times 10^{-12}$ to $1.75 \times 10^{-12}$ mole.

* * * * *